(12) United States Patent
Comiter et al.

(10) Patent No.: US 9,549,800 B2
(45) Date of Patent: Jan. 24, 2017

(54) IMPLANTABLE DEVICES FOR THE TREATMENT OF INCONTINENCE AND METHODS OF USING SAME

(71) Applicant: Coloplast A/S, Humlebaek (DK)

(72) Inventors: Craig Comiter, Palo Alto, CA (US); Eugene Rhee, San Diego, CA (US); Bryon Merade, Thousand Oaks, CA (US)

(73) Assignee: Coloplast A/S, Humlebaek (DK)

( * ) Notice: Subject to any disclaimer, the term of this patent is extended or adjusted under 35 U.S.C. 154(b) by 36 days.

(21) Appl. No.: 14/164,273

(22) Filed: Jan. 27, 2014

(65) Prior Publication Data

US 2014/0194676 A1    Jul. 10, 2014

Related U.S. Application Data

(63) Continuation of application No. 13/370,319, filed on Feb. 10, 2012, now Pat. No. 8,702,587, which is a continuation of application No. 12/445,849, filed as application No. PCT/US2007/081537 on Oct. 17, 2007, now Pat. No. 8,177,708.

(60) Provisional application No. 60/862,019, filed on Oct. 18, 2006.

(51) Int. Cl.
*A61F 2/02* (2006.01)
*A61F 2/00* (2006.01)

(52) U.S. Cl.
CPC .................... *A61F 2/0045* (2013.01)

(58) Field of Classification Search
CPC ...................................................... A61F 2/0045

USPC ....... 600/29, 30, 37; 606/151, 157; 128/885, 128/DIG. 25
See application file for complete search history.

(56) References Cited

U.S. PATENT DOCUMENTS

| | | | |
|---|---|---|---|
| 2,738,790 | A | 3/1956 | Todt, Sr. et al. |
| 5,284,141 | A | 2/1994 | Eibling |
| 5,899,909 | A | 5/1999 | Claren et al. |
| 5,934,283 | A | 8/1999 | Willem et al. |
| 6,042,534 | A | 3/2000 | Gellman et al. |
| 6,050,937 | A | 4/2000 | Benderev |
| 6,200,330 | B1 | 3/2001 | Benderev et al. |
| 6,273,852 | B1 | 8/2001 | Lehe et al. |

(Continued)

FOREIGN PATENT DOCUMENTS

| | | |
|---|---|---|
| RU | 2185779 C2 | 7/2002 |
| RU | 2243729 C1 | 1/2005 |

(Continued)

OTHER PUBLICATIONS

Almeida. Silvio H m. et al., "Use of Cadaveroc Facia Lata to Correct Grade IV Cystocle", Official Journal of the Brazilian Society of Urology, State University of Londrian, vol. 29, No. 1, Jan.-Feb. 2003, pp. 48-52.

(Continued)

*Primary Examiner* — Navin Natnithithadha
*Assistant Examiner* — Sunita Reddy
(74) *Attorney, Agent, or Firm* — Coloplast Corp., Coloplast A/S; Nick Baumann

(57) ABSTRACT

An implantable device includes a body member having a bottom side that is parallel to a top side; a pair of legs extending from the bottom side of the body member; and a pair of arms extending from the body member perpendicular to the pair of legs and a second arm extending from the body member perpendicular to the pair of legs.

10 Claims, 31 Drawing Sheets

(56) References Cited

U.S. PATENT DOCUMENTS

| | | |
|---|---|---|
| 6,302,840 B1 | 10/2001 | Benderev |
| 6,328,686 B1 | 12/2001 | Kovac |
| 6,491,703 B1 | 12/2002 | Ulmsten |
| 6,502,578 B2 | 1/2003 | Raz et al. |
| 6,638,211 B2 | 10/2003 | Suslian et al. |
| 6,666,817 B2 | 12/2003 | Li |
| 6,685,626 B2 | 2/2004 | Wironen |
| 6,808,486 B1 | 10/2004 | O'Donnell |
| 6,884,212 B2 | 4/2005 | Thierfelder et al. |
| 6,953,428 B2 | 10/2005 | Gellman et al. |
| 7,083,637 B1 | 8/2006 | Tannhauser |
| 7,393,319 B2 | 7/2008 | Merade et al. |
| 7,527,588 B2 | 5/2009 | Zaddem et al. |
| 7,878,969 B2 | 2/2011 | Chu et al. |
| 2001/0031973 A1 | 10/2001 | Nobles et al. |
| 2002/0099260 A1 | 7/2002 | Suslian et al. |
| 2002/0161382 A1 | 10/2002 | Neisz et al. |
| 2002/0188169 A1 | 12/2002 | Kammerer et al. |
| 2003/0023138 A1 | 1/2003 | Luscombe |
| 2003/0045774 A1 | 3/2003 | Staskin et al. |
| 2003/0171644 A1 | 9/2003 | Anderson et al. |
| 2003/0212305 A1 | 11/2003 | Anderson et al. |
| 2004/0039453 A1 | 2/2004 | Anderson et al. |
| 2004/0087970 A1 | 5/2004 | Chu et al. |
| 2004/0143152 A1 | 7/2004 | Grocela |
| 2004/0249240 A1 | 12/2004 | Goldmann et al. |
| 2004/0249473 A1 | 12/2004 | Delorme et al. |
| 2005/0027160 A1 | 2/2005 | Siegel et al. |
| 2005/0101834 A1 | 5/2005 | Merade |
| 2005/0240076 A1 | 10/2005 | Neisz et al. |
| 2006/0004246 A1 | 1/2006 | Selikowitz |
| 2006/0058575 A1 | 3/2006 | Zaddem et al. |
| 2006/0229493 A1 | 10/2006 | Weiser et al. |
| 2006/0229596 A1 | 10/2006 | Weiser et al. |
| 2006/0287571 A1 | 12/2006 | Gozzi et al. |
| 2007/0055095 A1 | 3/2007 | Chu et al. |
| 2008/0076963 A1 | 3/2008 | Goria |
| 2008/0210247 A1 | 9/2008 | De Leval |
| 2009/0048479 A1 | 2/2009 | Goria |
| 2009/0221868 A1* | 9/2009 | Evans ............. A61F 2/0045 600/37 |

FOREIGN PATENT DOCUMENTS

| | | |
|---|---|---|
| RU | 2275883 C2 | 5/2006 |
| WO | 2007137226 A2 | 11/2007 |

OTHER PUBLICATIONS

Chon, J et al., "Results of the Transvaginal Cadaveric Prolapse Repair with Sling (CAPS)", International Urogyn Journal, 2002 13(1):S40, abstract #70 presented at International Urogynecology Association, 27th Annual meeting. Prague Czech Republic, Aug. 24, 2002, 1 page.

Kobashi, Kathleen C. et al., "A new Technique for Cystocele Repair and Transvaginal Sling: The Cadaveric Prolapse Repair and Sling (CaPS)", Elsevier Science Inc., Dec. 2000, pp. 9-14.

Kobashi, Kathleen et al., "The use of Solvent-Dehydrated Cadaveric Facia Lata (tutoplast) in Slings and Cystocele Repairs: The Virginia Mason Experience", International Urigyn Journal, 2002 13(1)S35. abstact #130, Presented at International Urogyecology Association, Prague Czech Republic, Aug. 24, 2002, 2 pages.

* cited by examiner

IMPLANTABLE DEVICES FOR THE TREATMENT OF INCONTINENCE AND METHODS OF USING SAME

FIELD OF THE INVENTION

The present invention relates generally to surgically implantable devices and methods for the treatment of incontinence. The invention relates more particularly to (i) implantable devices that are designed to provide support to the bulbar urethral region of a male patient, (ii) surgical methods of implanting the devices, and (iii) surgical tools for use with the surgical methods.

BACKGROUND OF THE INVENTION

Of the estimated 19 million North American adults who have urinary incontinence, 20% are estimated to be men. Such condition can range in severity from partial to complete loss of bladder control and patients afflicted with urinary incontinence can experience varying degrees of urine loss. In addition, it is known that urinary incontinence may change over time and that men and women with light incontinence, for example, may experience minimal leakage during the occurrence of a provocative event, such as laughing or coughing, whereas men with heavy incontinence may experience continuous urine leakage.

Generally, urinary incontinence is not considered a disease, but rather a symptom or side effect of another medical condition. Some conditions known to cause male urinary incontinence include prostate surgery, and in particular total prostatectomy, head and spinal cord injury, infection, certain toxins, such as too much alcohol consumption, certain medications, such as sedating medications, and certain diseases, such as cancer, Parkinson's disease and multiple sclerosis. Indeed, male incontinence can be caused simply by virtue of the aging process or emotional distress.

Each case of incontinence, however, is unique and no two people are affected by incontinence in the same way. There are, however, well-recognized types of incontinence and various ways to treat the same. Stress incontinence, which is a common type of incontinence, may be characterized as urine leakage during a provocative event such as sneezing, laughing, lifting heavy objects, or when the patient engages in any type of exercise that puts pressure on the bladder. Urge incontinence occurs when the patient wants to urinate but is incapable of exercising restraint until reaching a restroom. Additional types of incontinence include overflow incontinence, which occurs when the quantity of urine exceeds the capacity of the patient's bladder, and functional incontinence, which occurs when the patient has knowledge of the need to urinate but simply cannot access a restroom quickly enough due to a physical obstruction or debilitation.

To treat urinary incontinence, several options are available. Among the more effective types of recognized treatment include behavioral techniques, such as biofeedback, bladder training, and pelvic muscle exercises, and modifications of the patient's diet and fluid intake. With respect to the latter, it is known that eliminating or cutting back on certain types of substances, such as caffeine and alcohol, can help alleviate incontinence. There are additionally medications available, such as dicyclomine (Bentyl), flavoxate (Urispas), hyoscyamine sulfate (Anaspaz), imipramine (Tofranil), oxybutynin (Ditropan), tolterodine (Detrol), and propantheline (Pro-Banthine), phenylpropanolamine (Dexatrim), and pseudoephedrine (Sudafed) that are helpful in controlling urinary incontinence.

Surgery may additionally be an option to treat male urinary incontinence. Along these lines, surgically implantable devices for males, such as the In-Vance sling device and Artificial Urinary Sphincter (AUS), produced by American Medical Systems, Inc., of Minneapolis, Minn. The InVance sling device is a commercially available surgically implantable device that is operative to provide structural support to the urethra for the treatment of stress incontinence. In this regard, the device is operative to provide structural support to the urethra such that during a provocative event, the device will provide structural support to the urethra thus causing the urine to be retained within the bladder and not leak through the urethra. The AUS is a fluid-filled cuff that surrounds the urethra and keeps it closed. While both devices have been used in the treatment of incontinence, they are not easily used by the average urologist. For example, there are issues with the patient not being 100% dry postoperatively due to the sling or AUS being too loose. Alternatively, there are also issues with patients being put in retention postoperatively due to the device being too tight.

Utilizing such sling devices to treat incontinence has been known to have numerous additional drawbacks. For example, securing suburethral sling devices into position typically requires the use of bone screws, which are well-known in the art to be difficult and time consuming to deploy, and can result in significant patient discomfort, especially within the first couple of weeks following the surgical implantation.

In addition, procedures and methods for implanting suburethral sling devices often lead to difficulties in securing them into position with optimal degrees of tension. Indeed, the implantation of suburethral sling devices for the treatment of incontinence may be complex and time consuming, and may produce suboptimal clinical outcomes. Moreover it is recognized among surgeons who perform such implant procedures that sutures attached to bone anchors or bone screws, which are utilized to secure the devices into position, frequently break and that often times additional bone anchors or screws must be secured into position. In fact, sutures attached to bone anchors and or bone screws usually need to be individually re-tensioned several times before optimal device positioning and structural support to the urethra is achieved.

Accordingly, there is a substantial need in the art for a suburethral implantable device for the treatment of incontinence that may be easier to surgically secure into position and that may further provide an optimal degree of urethral support to thus effectively treat urinary incontinence. There is additionally a need in the art for an implantable device that may be simply constructed, easy to surgically manipulate, and which may be manufactured at relatively low cost utilizing known implant materials—whether they are synthetic materials, natural tissues, or combinations thereof. There is yet a further need in the art for such an implantable device that can be secured into position such that the device defines a suburethral portion operatively positioned to support the bulbar urethral region of the patient, with the device remaining in position via use of at least a pair of elongated extension members, such as arms, that are secured at or near respective pubic rami (variously referred to in the art as pubic rami/ramus (plural/singular) or descending pubic rami/ramus (plural/singular)—which surround or define the obturator foramen of a patient's pelvic region) without the use of bone anchors. With respect to the latter, it would be advantageous for such an implantable device to be secured, at least in part, by way of obturator foramen and preferably via pubic rami thereof. There is also a need for an implantable device that provides an opportunity to adjust tensioning of the implanted device postoperatively, in a minimally invasive and efficient manner.

SUMMARY OF THE INVENTION

One object of the present invention is to address and alleviate the aforementioned deficiencies in the medical art. In this regard, it is another object of the present invention to provide surgically implantable devices, surgical methods, and surgical tools that are effective and are substantially easier to use than known implants, methods, and tools for treating incontinence.

In accordance with one aspect of the present invention, novel implantable devices are designed to provide support to the bulbar urethral region of a male patient, novel surgical methods are utilized to implant the devices, and novel surgical tools are utilized with the surgical methods.

In one aspect of the invention an implantable device is disclosed. The implantable device comprises a body member, at least first and second elongated extension members extending from the body member toward respective first and second ends with the first and second elongated extension members extending laterally away from the body member on opposite sides, at least third and fourth elongated extension members extending from the body member toward respective third and fourth ends with the third and fourth elongated extension members extending longitudinally away from the body member. This provides implantable devices for treating urinary incontinence which have shapes that may be well suited for the methods disclosed herein. E.g., lateral extensions of the first and second elongated extension members (also referred to as the "arms" of the devices herein) allow the arms to be easily fixed around the pubic rami without folding, bulging, or otherwise deforming the material of the device; this may be important because if the device unintentionally folds, bulges, or otherwise deforms upon implantation, discomfort to the patient may result and desired urethral compression may be compromised as the folding, bulging, or deformation exerts unexpected and undesired internal pressures. Likewise, longitudinal extensions of the third and fourth elongated extension members (also referred to as the "legs" of the devices herein) allows the legs to be easily and directly guided up to abdominal or suprapubic incisions (as disclosed below with respect to the surgical methods) without the aforementioned deformation effects.

In a further embodiment of the implantable device, the first and second elongated extension members (i.e., the arms of the device) are attached to each other, and/or the third and fourth extension members (i.e., the legs of the device) are attached to each other. Thus by attaching two arms together, only one suture (or other means for attachment) may be necessary which makes the procedure less complicated. By attaching two legs to each other there may be only one "pull point", which in turn may better facilitate adjustment of tension of the device both during surgery and postoperatively. As described herein the attachment point of the legs may not necessarily be placed symmetrically, but may be offset to one side—which therefore could make a distance from the body member of the device to the attachment point of one leg shorter relative to the other. This has the effect that the surgeon can make a suture (or other suitable attachment means) in a vicinity of one of the abdominal or suprapubic incisions instead of under the skin or deeper within the patient. The effect of, in an example embodiment, attaching the arms to each other and the legs to each other serve two separate and distinct purposes, as will be understood. Thus, an embodiment where, for example, the arms are separately attached to the body member of the device or back to the arms themselves while the legs are attached to each other may also be provided.

Using regular square or rectangular elements for the body member of the implant often results in folding, bulging, or other deformation of the device which as described previously may result in discomfort to the patient and compromise the desired urethral compression. Depending on the surgical method utilized, devices may deform differently and thus some implantable device shapes are preferred in one method while the same shapes might not be optimal in other methods. It has therefore been found that for surgical methods disclosed herein, it may be advantageous for an implantable device of the present invention to have a body member having: a trapezoidal shape, at least first and second elongated extension members extending from and in parallel with a top of the trapezoidal shape of the body member, and at least third and fourth elongated extension members extending from and transverse to a bottom of the trapezoidal shape of the body member.

In another embodiment of the invention, a sleeve may cover the implantable device. Such a sleeve may facilitate placement of the device, and may also function as a barrier to contamination of the device. The sleeve could also protect the patient's body tissues against erosion or other detrimental frictional effects during placement of the device. Such a sleeve may, for example, be produced of a high-density polyethylene with a thickness of 4 mil (0.1016 mm).

In a further embodiment, tubing may be fixed over selected ones of the at least first, second, third, and fourth ends of the implantable device. Such tubing, selectively coupled to the device, may provide tapering ends (in some embodiments the ends themselves may be tapered as will be described) which facilitates easier passage through the patient's body while inserting the implantable device. The tubing may be arranged on a sleeve, thus aiding in holding the sleeve in place on the device. The tubing may be heat shrunk and, for example, be formed of polyolefin with a length of 13 mm+/−1 mm. While heat shrinking the tubing, suture attachments may be knotted or otherwise secured to proximal first halves of the tubing. In one embodiment such sutures may be braided sutures of 0 size, with a diameter between 0.350 mm and 0.399 mm. A nominal working length of the sutures may be, for example, 22.5 cm.

The implantable device may be formed of a mesh; in one example it may be warp knitted from 7.5 mil monofilament polypropylene. At least first and second ends of at least first and second elongated extension members (i.e., the arms) may have mesh tapers from 1.5 cm to 0.6 cm. This tapering may facilitate smooth passages into the patient's body tissues.

In another aspect of the invention, an introducer is disclosed for introducing an implantable device into the human body. The introducer may comprise a hook shaped guide curving in one plane from a handle to an introducer tip, where the curvature may allow the introducer to be placed around the pubic rami by starting from within a perineal incision. This may allow the surgical method to be performed without an additional perineal incision, thereby reducing a duration of the implantation surgery while also reducing discomfort to the patient.

In one embodiment of such an introducer, which may allow the surgeon to use just one perineal incision, a curvature of the hook shaped guide may be between 220 and 240 degrees; it may preferably be between 225 and 235 degrees; and it may in particular be 229 degrees.

In another aspect of the invention, a suprapubic introducer is also disclosed for introducing an implantable device into the human body. The suprapubic introducer may comprise a curved body extending from a handling end to an introducer tip, where the curvature of the curved body may be adapted so that the introducer tip of the suprapubic introducer may be passed prepubically from above, through a suprapubic or abdominal incision and passed out through the perineal incision.

In alternative embodiments of both the introducer and suprapubic introducer of the present invention, the introducer tips thereof include a slot for receiving a suture loop therein.

In another aspect of the invention, a method for treating urinary incontinence is disclosed. In the method, an implantable device may be provided having a body member including a top and a bottom, at least first and second elongated extension members and at least third and fourth elongated extension members. The patient may be placed in a lithotomy position. A vertical perineal incision in a midline may be made, dissecting laterally to expose periutheral fat above a bulbar urethral complex of the patient and down to pubic rami bilaterally leaving periutheral tissue intact. A first introducer may be provided having an introducer tip. The first introducer may be placed around a first pubic ramus by starting from within the vertical perineal incision from outside-in, medially, and through an obturator membrane corresponding to the first pubic ramus. The introducer tip of the first introducer may be guided through an obturator foramen corresponding to the first pubic ramus. One of the at least first and second elongated extension members may be attached to the introducer tip of the first introducer. The first introducer may then be pulled back out by reversing a path that the first introducer had followed from outside-in until the one of the at least first and second elongated extension members is free and may be grasped. The first introducer may then be placed around a second pubic ramus by starting from within the vertical perineal incision from outside-in, medially, and through an obturator membrane corresponding to the second pubic ramus. The introducer tip of the first introducer may then be guided through an obturator foramen corresponding to the second pubic ramus. Another of the at least first and second elongated extension members may then be attached to the introducer tip of the first introducer. The first introducer may then be pulled back out by reversing a path that the first introducer had followed from outside-in until the another of the at least first and second elongated extension members is free and may be grasped. The at least first and second elongated extension members may be pulled so that the bottom of the body member is placed just inferior to a level of the bulbar urethral complex and over a pubic symphysis of the patient, superiorly. The at least first and second elongated extension members, that extend through each of said obturator foramen, may be sutured to each other. An opposing pair of abdominal incisions may be made above the pubic symphysis and lateral to the midline. A second introducer may be provided, having a curved body extending from a handling end to an introducer tip. The second introducer may be passed, prepubically from above, to enter a first of the pair of abdominal incisions and pass out through the perineal incision lateral to the periutheral tissue. One of the at least third and fourth elongated extension members may be attached to the second introducer. The second introducer may then be pulled back out by reversing a path that the second introducer had followed and out from the first abdominal incision. The second introducer may then be passed, prepubically from above, to enter a second of the pair of abdominal incisions and pass out through the perineal incision lateral to the periutheral tissue. Another of the at least third and fourth elongated extension members may then be attached to the second introducer. The second introducer may then be pulled back out by reversing a path that the second introducer had followed and out from the second abdominal incision. Selected ones of the at least third and fourth elongated extension members may then be pulled such that the body member of the implantable device is over the patient's pubic symphysis, superiorly. The at least third and fourth elongated extension members may then be secured within the patient's body.

In one embodiment of such a method, the step of securing the at least third and fourth elongated extension members within the patient's body may include passing a selected one of the at least third and fourth elongated extension members under the patient's skin to a vicinity of another of the at least third and fourth elongated extension members. The another of the at least third and fourth elongated extension members may then be anchored, subcutaneously, below the level of the patient's skin. The at least third and fourth elongated extension members may then be tied together.

In another embodiment of such a method, the step of securing the at least third and fourth elongated extension members within the patient's body may include passing a selected one of the at least third and fourth elongated extension members under the patient's skin to a vicinity of another of the at least third and fourth elongated extension members. The another of the at least third and fourth elongated extension members may then be anchored, subcutaneously, below the level of the patient's skin. The at least third and fourth elongated extension members may then be sutured together.

In yet another embodiment of such a method, the step of securing the at least third and fourth elongated extension members within the patient's body may include passing a selected one of the at least third and fourth elongated extension members under the patient's skin to a vicinity of another of the at least third and fourth elongated extension members. The another of the at least third and fourth elongated extension members may then be anchored, subcutaneously, below the level of the patient's skin. The at least third and fourth elongated extension members may then be sutured to the body member of the implantable device.

In yet another embodiment of such a method, the step of securing the at least third and fourth elongated extension members within the patient's body may include passing a selected one of the at least third and fourth elongated extension members under the patient's skin to a vicinity of another of the at least third and fourth elongated extension members. The another of the at least third and fourth elongated extension members may then be anchored, subcutaneously, below the level of the patient's skin. The at least third and fourth elongated extension members may then be left within the patient's body cavity, thereby engaging surrounding tissue and permitting fibroblast infiltration to further tension and secure the at least third and fourth elongated extension members within the patient's body cavity.

BRIEF DESCRIPTION OF THE DRAWINGS

Other features and advantages of the present invention will be seen as the following description of example embodiments in conjunction with the drawings, in which.

DETAILED DESCRIPTION OF THE INVENTION

Figure 1:
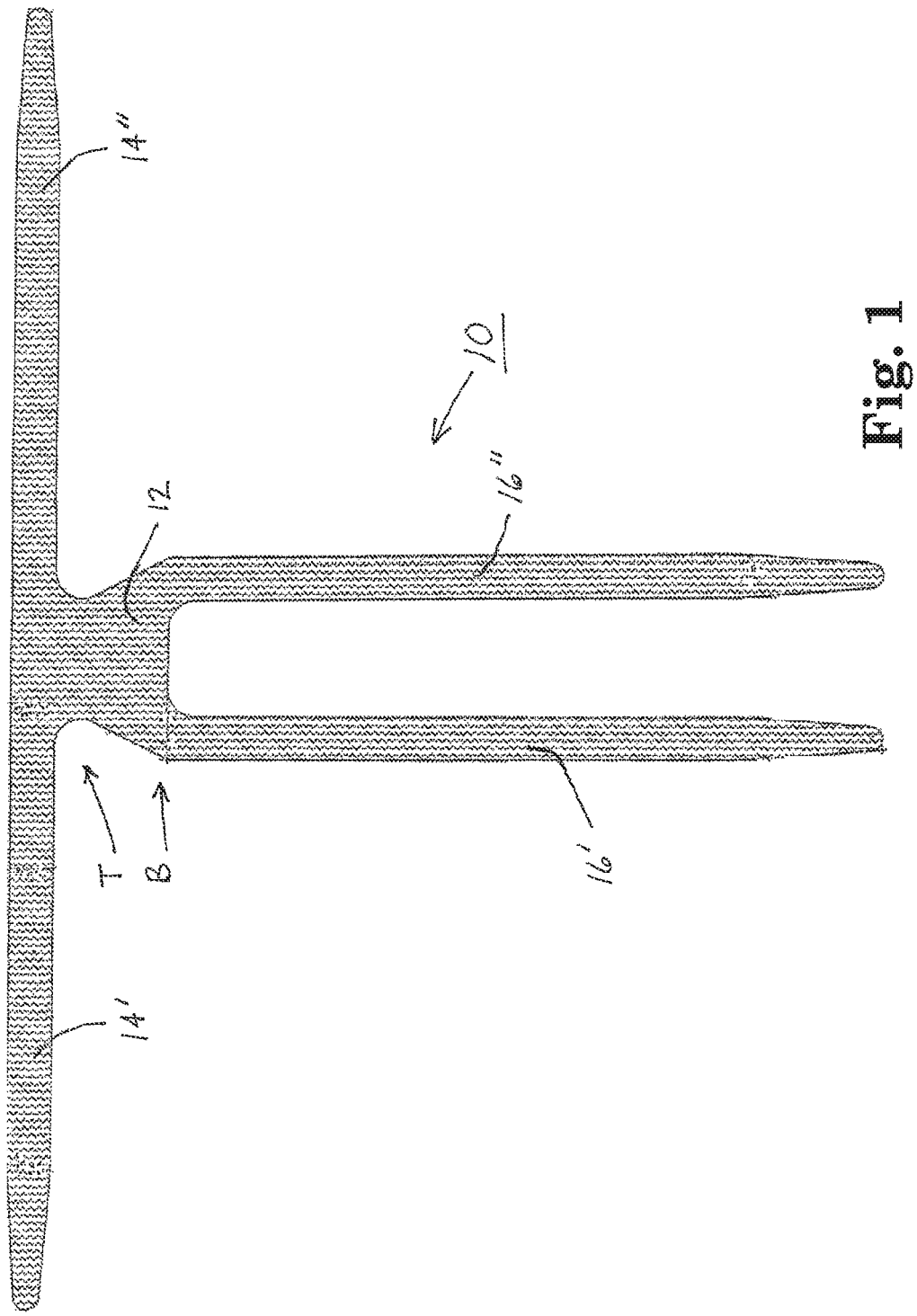
FIG. 1 is an illustration of an example of an implantable device of the present invention.

One embodiment of an implantable device 10 (or, "device 10") as contemplated for use with the present invention, as illustrated in FIG. 1, includes a body member 12, a first elongated extension member or arm 14', a second elongated extension member or arm 14", a third elongated extension member or leg 16', and a fourth elongation extension member or leg 16". These components are placed in such an orientation as to provide both anchoring and support to the bulbar urethral complex of a male patient.

In one preferred embodiment of the invention, the body member 12 may be formed substantially in the shape of a trapezoid, with arms 14', 14" extending substantially laterally away from a narrow end of the trapezoid and away from one another, and legs 16', 16" extending longitudinally away from a wide end of the trapezoid in substantially parallel relation to one another. It is to be understood, however, that legs 16', 16" may be in any orientation with respect to each other, whether parallel, substantially so, or not parallel at all. Ultimately, orientation of the at least third and fourth elongated extension members may be chosen with respect to suitability for each patient's unique anatomy. In summary, then, the arms 14', 14" extend from a top T of the trapezoidal body member 12 and the legs 16', 16" extend from a bottom B of the trapezoidal body member 12.

The angles and dimensions of the trapezoidal body member 12 may vary depending on the type of material and on the particular anatomy of the patient receiving the device. Thus it should be understood that the tapering end (top) T of the trapezoid, from where the arms 14', 14" extend, should fit between the pubic rami. In this regard, it will be appreciated that if the width of the tapering end exceeds a width between the pubic rami, then there is a risk that the material of the device 10 could fold, bulge, or otherwise deform and thus compromise the success of the surgery as described above. However, the widest end of the trapezoid (bottom) B of the body member 12 serves to support the bulbar urethral complex; thus, the larger surface (relative to the top of the trapezoid) evenly distributes pressure and provides a desirable compression of the urethral complex.

Materials suitable for use in constructing the device 10 of the present invention may include synthetic materials such as meshes and the like, natural tissues such as tissues harvested from an animal, a cadaverous source, or the patient himself, or any suitable combinations of synthetic and natural materials.

The implantable device 10 illustrated in FIG. 1 may be, for example, fabricated from a mesh. The mesh may be warp knitted from 7.5 mil monofilament polypropylene. Table 1 shows example specifications of such a mesh formed in accordance with the device 10 illustrated in FIG. 1.

TABLE 1

| | |
|---|---|
| WPI | 17 |
| CPI | 41 |
| Thickness | 0.0251" |
| Density | 146.3 (g/m2) |
| Pore Size | 0.4419 (mm2) |
| Burst Strength | 149.991 (lbf) |
| Tensile strength, Machine Direction | 92.608 (lbf) |
| Tensile strength, Cross Direction | 90.894 (lbf) |
| Stiffness, Machine Direction | 2.91 (cm) |
| Stiffness, Cross Direction | 3.70 (cm) |

Figure 2:
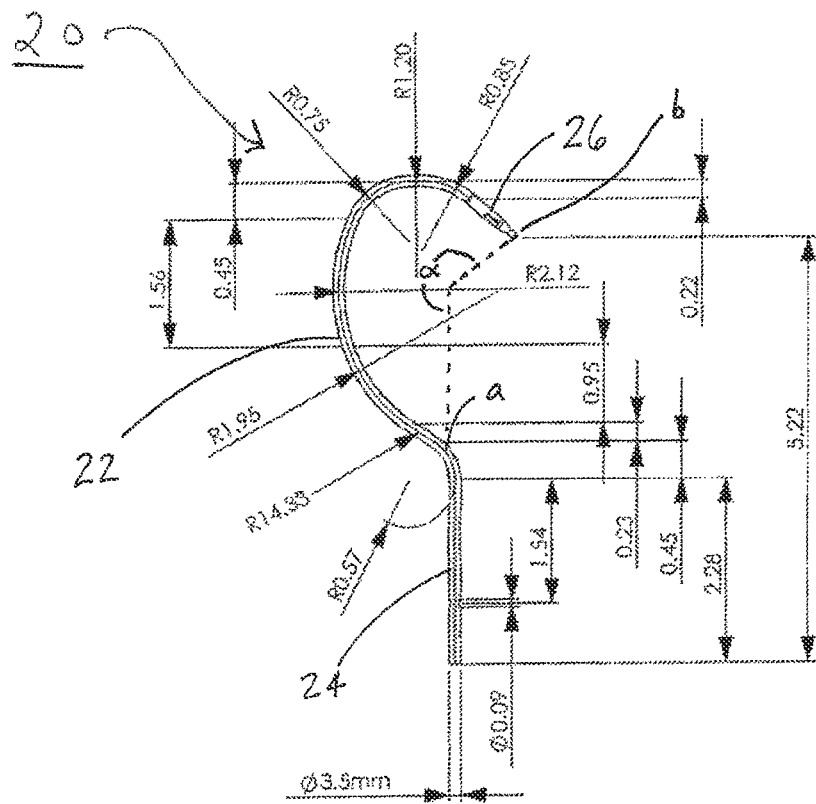
FIG. 2 is an illustration of an example of an introducer of the present invention.

An introducer 20 that may be suitable for placing the arms 14', 14" of the device 10 through the obturator foramen with the example surgical method disclosed below is shown in FIG. 2.

The introducer 20 has a hook shaped guide 22 extending from point 'a' on the end of a shaft 24 of the introducer 20 to point 'b' on an introducer tip 26. The tip 26 may include a recessed aperture or slot as described below. The hook shaped guide 22 may have a curvature a from point 'a' to 'b' of 229 degrees. The hook shaped guide 22 terminates at point 'b' in the introducer tip 26, which is adapted to be attached to the arms and legs of the device. The curvature of the hook shaped guide 22 may be provided in many different forms as may be desired for particular surgeries. In the example embodiment shown in FIG. 2, the hook shaped guide 22 can be seen as being divided into six segments having different radii. Table 2 gives an overview of these segments extending from point 'a' to point 'b' with reference to their radii over an extent parallel to the shaft 24 of the introducer 20.

TABLE 2

| Segment # | Radius (in.) | Length (in.) (parallel to the shaft) |
|---|---|---|
| 1 | 14.33 | 0.23 |
| 2 | 1.95 | 0.95 |
| 3 | 2.12 | 1.56 |
| 4 | 0.75 | 0.45 |
| 5 | 1.20 | 0 (apex of the curvature) |
| 6 | 0.85 | 0.22 |

It should be understood that the dimensions set out in Table 2 are of but one example embodiment. Thus, other dimensions may be provided for the introducer 20 within the scope of the invention. To provide a good grip for the surgeon in use of the introducer 20, a handle (not shown) may be attached to the shaft 24 of the introducer.

Figure 3:
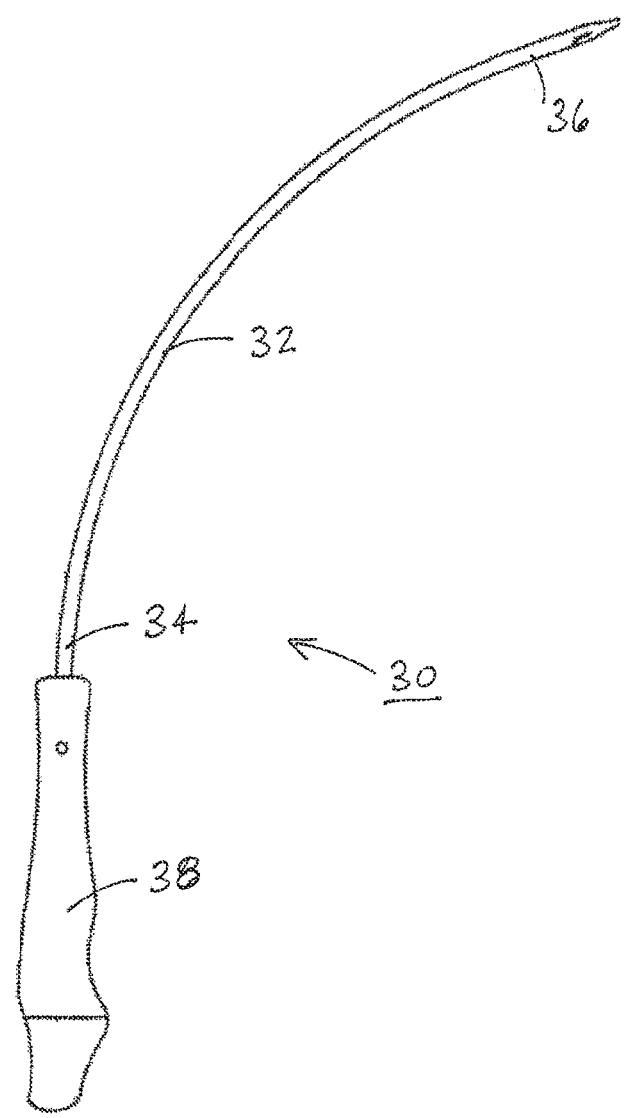
FIG. 3 is an illustration of an example of a suprapubic introducer of the present invention.

A suprapubic introducer 30 for arranging the legs 16', 16", again with the example surgical method disclosed below, is shown in FIG. 3. The suprapubic introducer may be formed of a curved body 32 extending from a handling end 34 to an introducer tip 36. The tip 36 may be adapted to be attached to the elongated extension members 16', 16". Like tip 26 of introducer 20, the tip 36 of suprapubic introducer 30 may also include a recessed aperture or slot as described below. The curvature of the curved body 32 of the suprapubic introducer 30 may be adapted so that it may be passed prepubically from above, through an abdominal incision and passed out through a perineal incision as will be described below. A handle 38 may be provided at the handling end of the suprapubic introducer 30. The handle may be detachable or fixed to the handling end 34.

Figure 3A:
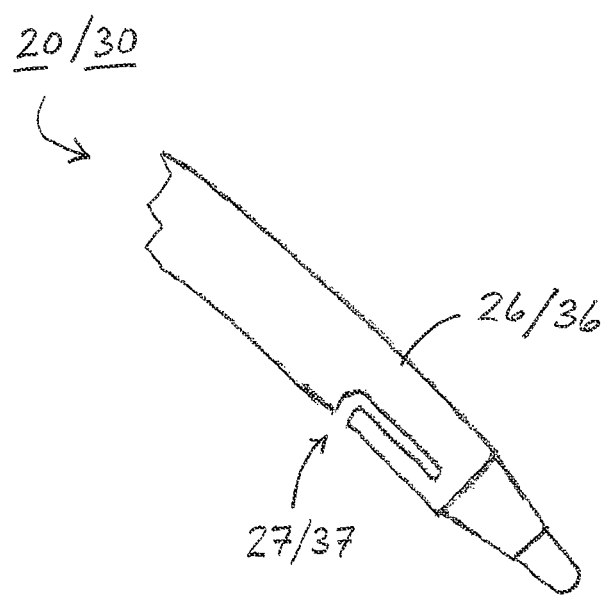
FIG. 3a is a magnified illustration of a specific feature of the introducers shown in FIGS. 2 and 3.

Turning, now, to FIG. 3a, the aforementioned recessed aperture or slot in the tips 26/36 of the introducers 20/30, respectively, is shown in a magnified illustration. The recessed aperture or slot 27/37 in the introducers 20/30, respectively, is designed to securely, although temporarily, hold a suture therein. Such a suture could be fashioned as a loop and secured (whether permanently or temporarily) to an end of the elongated extension member. With this feature 27/37, it is to be appreciated that the introducer tips 26/36 may readily capture or "grab" the suture loop to facilitate pulling of the suture and the end of the elongated extension member to which it is attached. Thus, as aforementioned in summary above, the introducer 20/30 may then be pulled back out by reversing a path that the introducer had followed until the elongated extension member is free and may be grasped. Finally, the elongated extension member can be disconnected from the introducer by removing the suture loop from the slot.

Referring now to FIGS. 4-30, therein illustrated is one example of implantable devices of the present invention—namely, the aforedescribed device 10—utilizing examples of surgical methods and surgical tools of the present invention. Such devices, methods, and tools provide examples that may be used in the treatment of incontinence. In the drawings, it will be appreciated that a model of a pelvic region including pelvic bone structure is shown.

Figure 4:
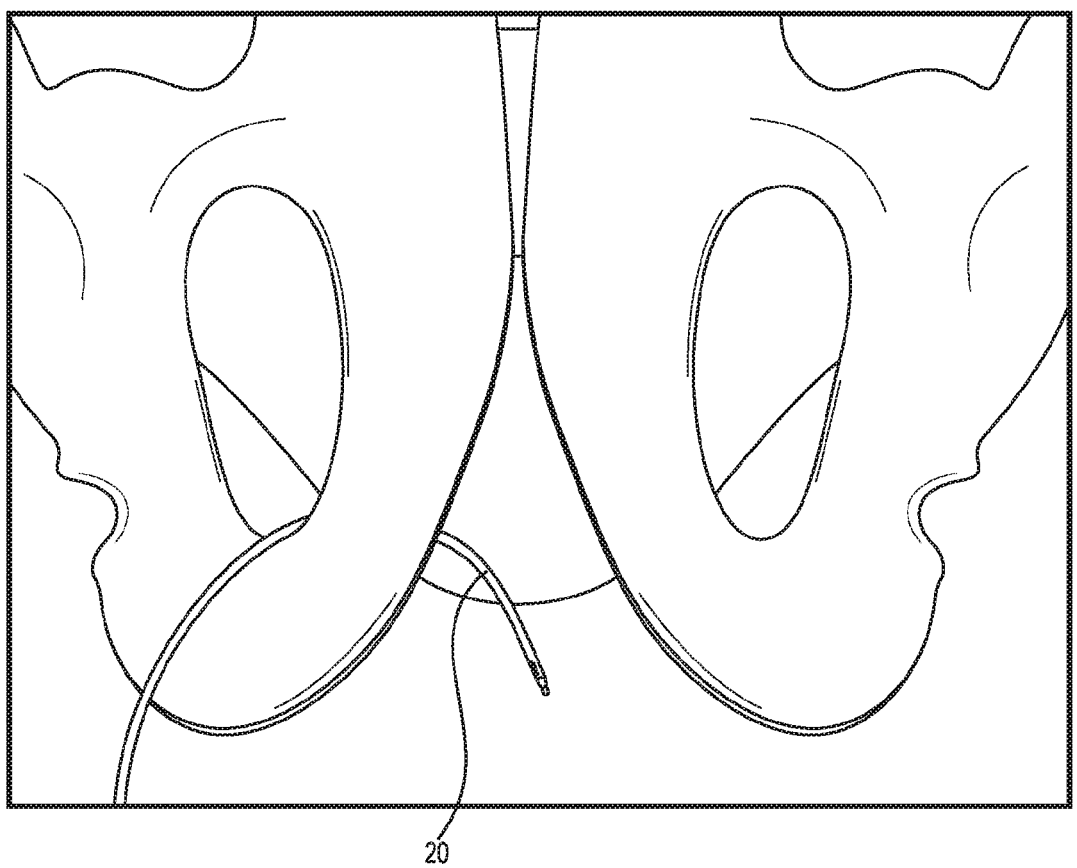
FIGS. 4-30 are illustrations showing various steps of an example of a surgical implantation method of the present invention.

One technique of placing the device 10 in a patient by a surgeon as contemplated within the present invention includes an example surgical method as follows. The patient may be placed in a slightly exaggerated lithotomy position. A 16 Fr foley catheter may be placed. A vertical perineal incision may be made in the midline, dissecting to expose the periurethral fat above the bulbar urethra of the patient. The dissection may be performed laterally down to the pubic rami bilaterally leaving the periurethral tissue intact. The foley catheter may be palpated deep posteriorly. An introducer 20, preferably having a dimension and structure sufficient to place selected portions of the device 10 through the obturator foramen, at least in part within the perineal incision, may be provided and passed from either outside-in or inside-out along the medial aspect of the palpated obturator foramen of the patient, at a level just superior to the bulbar urethral complex via the perineal incision. More specifically, as shown in FIG. 4, the introducer 20 may be placed around the pubic ramus by starting from within the perineal incision from outside-in medially. Care should be taken to palpate the tip of the introducer 20 with the surgeon's non-dominant hand as the surgeon feels an initial "pop" through the obturator membrane.

Figure 5:
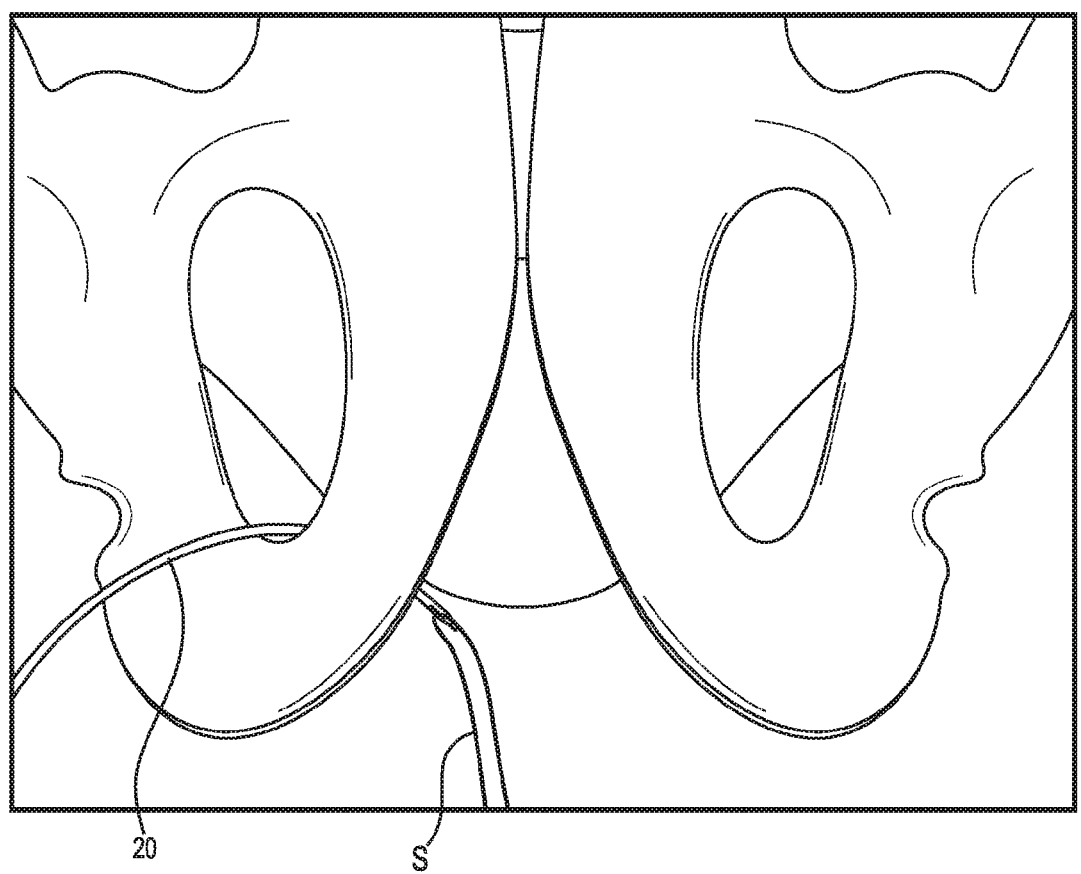
Figure 6:
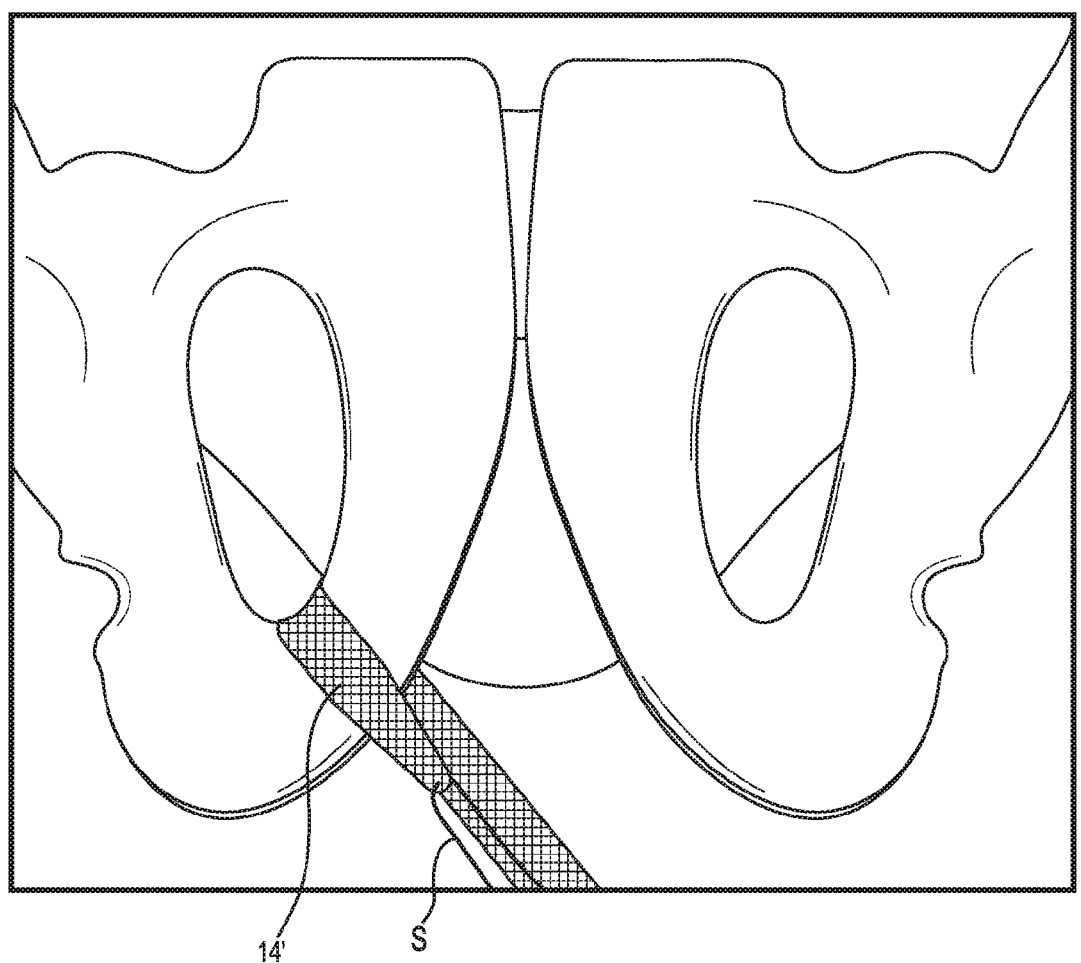
Figure 7:
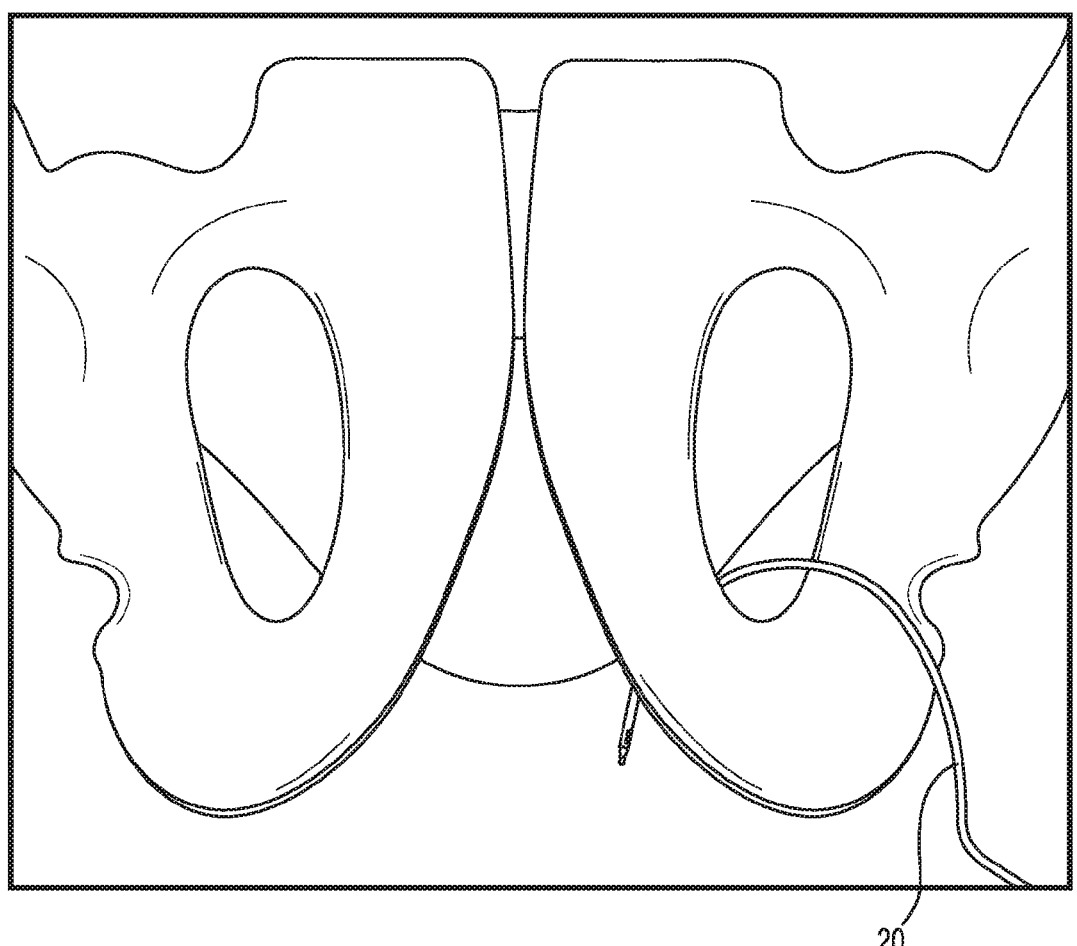
Figure 8:
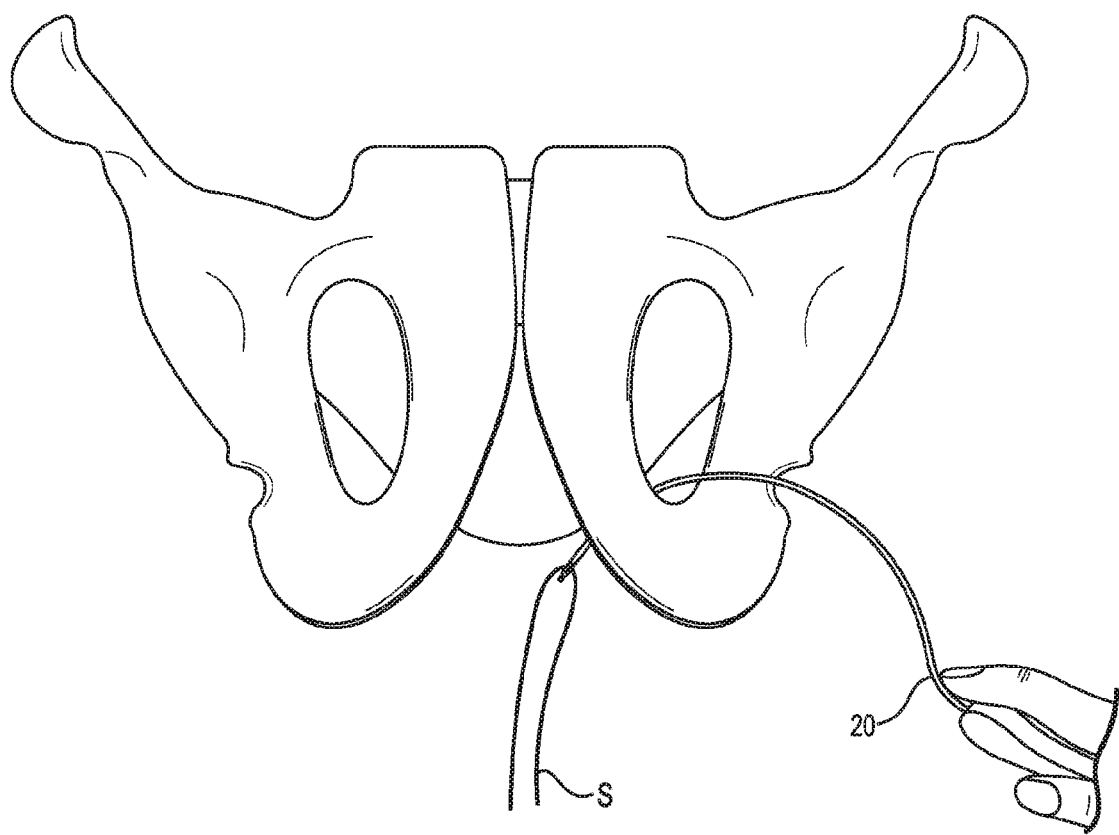
Figure 9:
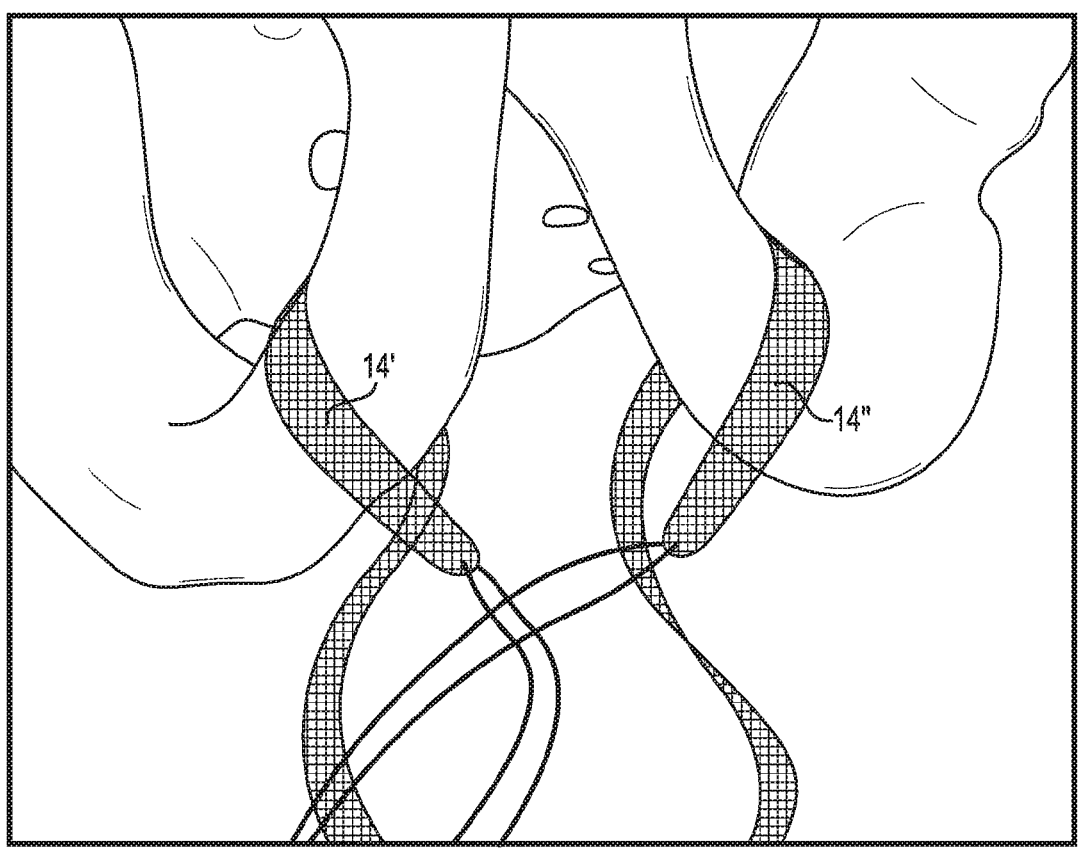

The introducer 20 may be guided against the bone of the pubic ramus as the introducer tip 26 may be visualized emanating from the inferior and medial aspect of the obturator foramen. As shown in FIGS. 5 and 6, the arm 14' of the device 10 may be attached to the introducer 20, preferably by loading a suture S with the arm 14' or by any suitable technique of attaching the arm 14' to a portion proximal to the introducer tip 26 (e.g., by way of the aforedescribed slot 27) and pulled back out by reversing the pathway that the introducer 20 entered until the arm 14' may be free and can be grasped. As shown in FIGS. 7, 8, and 9, these steps are repeated on the contra lateral side, with respect to the arm 14".

Figure 10:
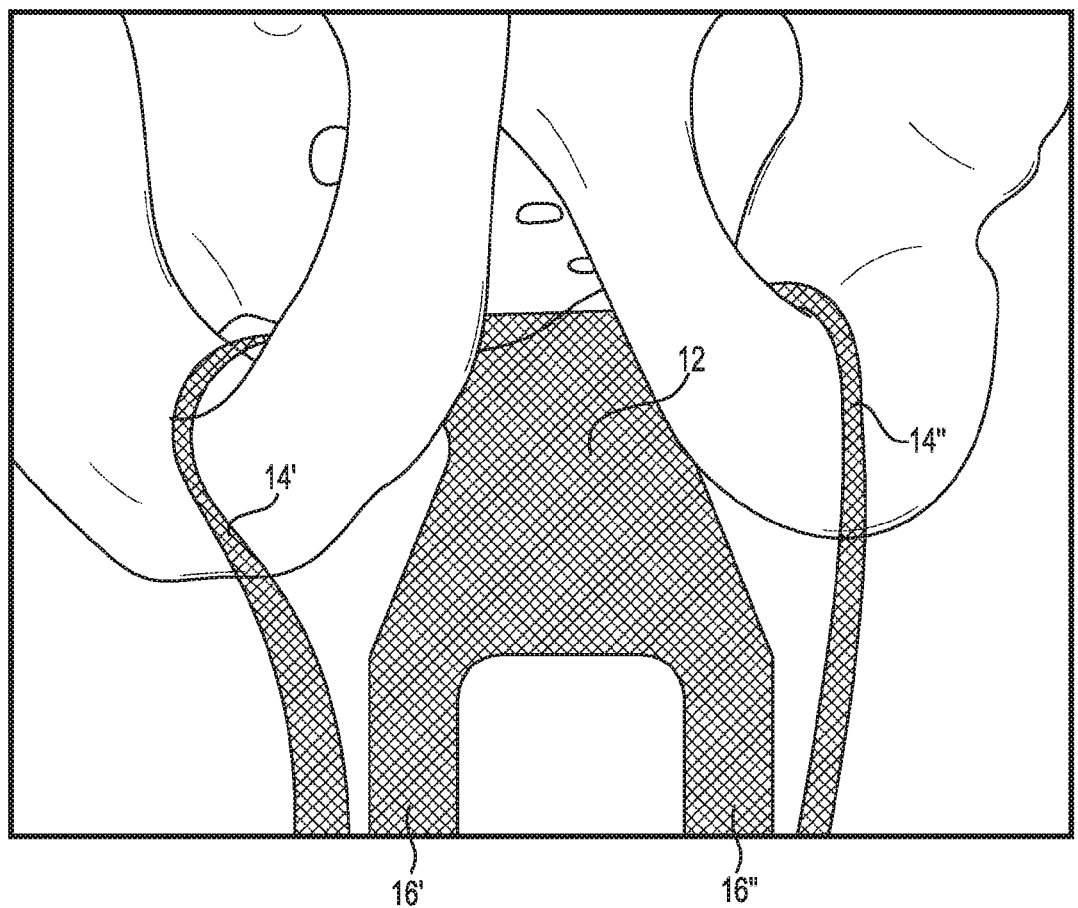
Figure 11:
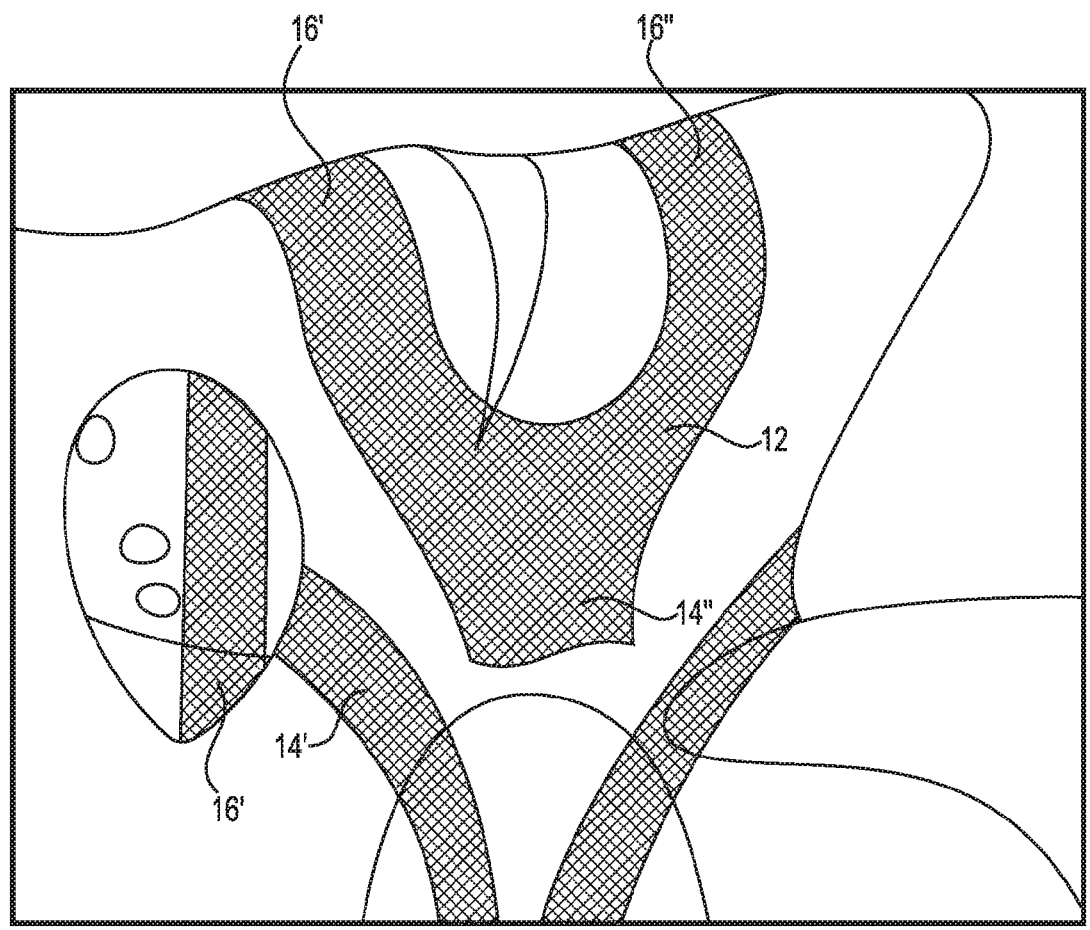
Figure 12:
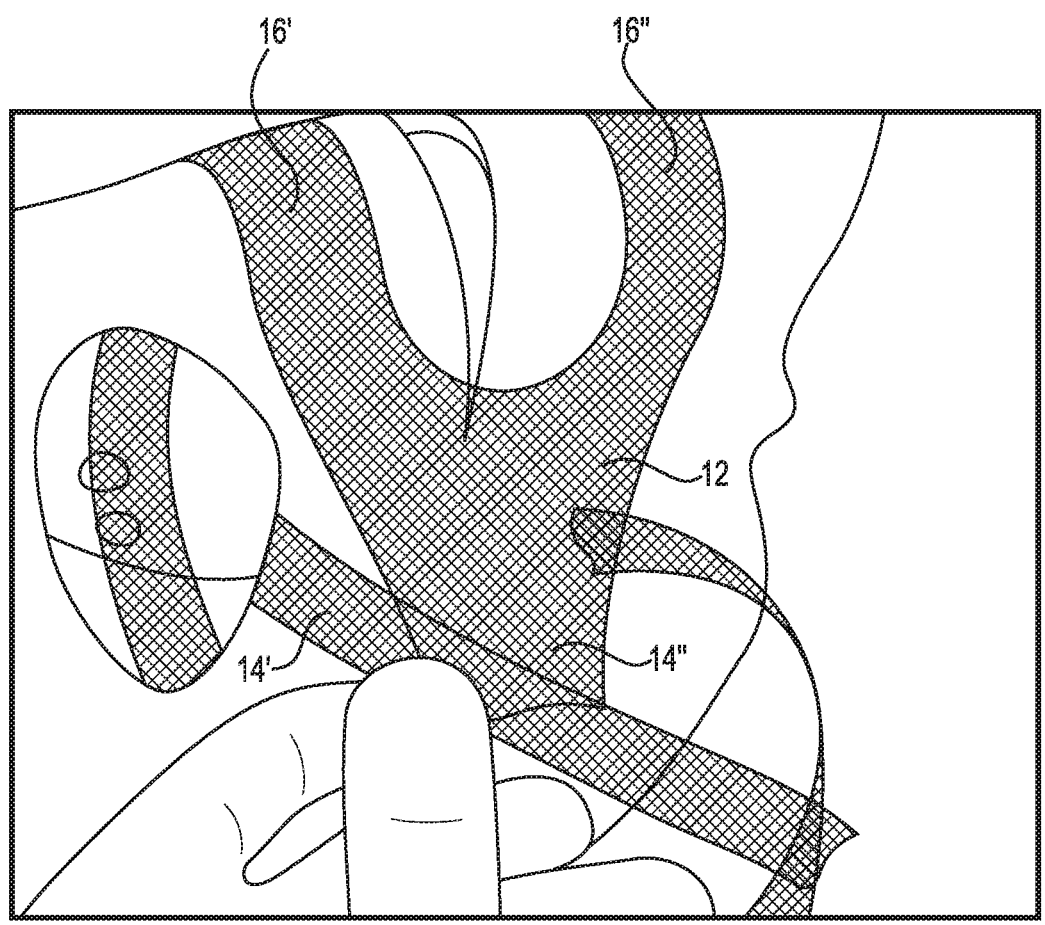
Figure 13:
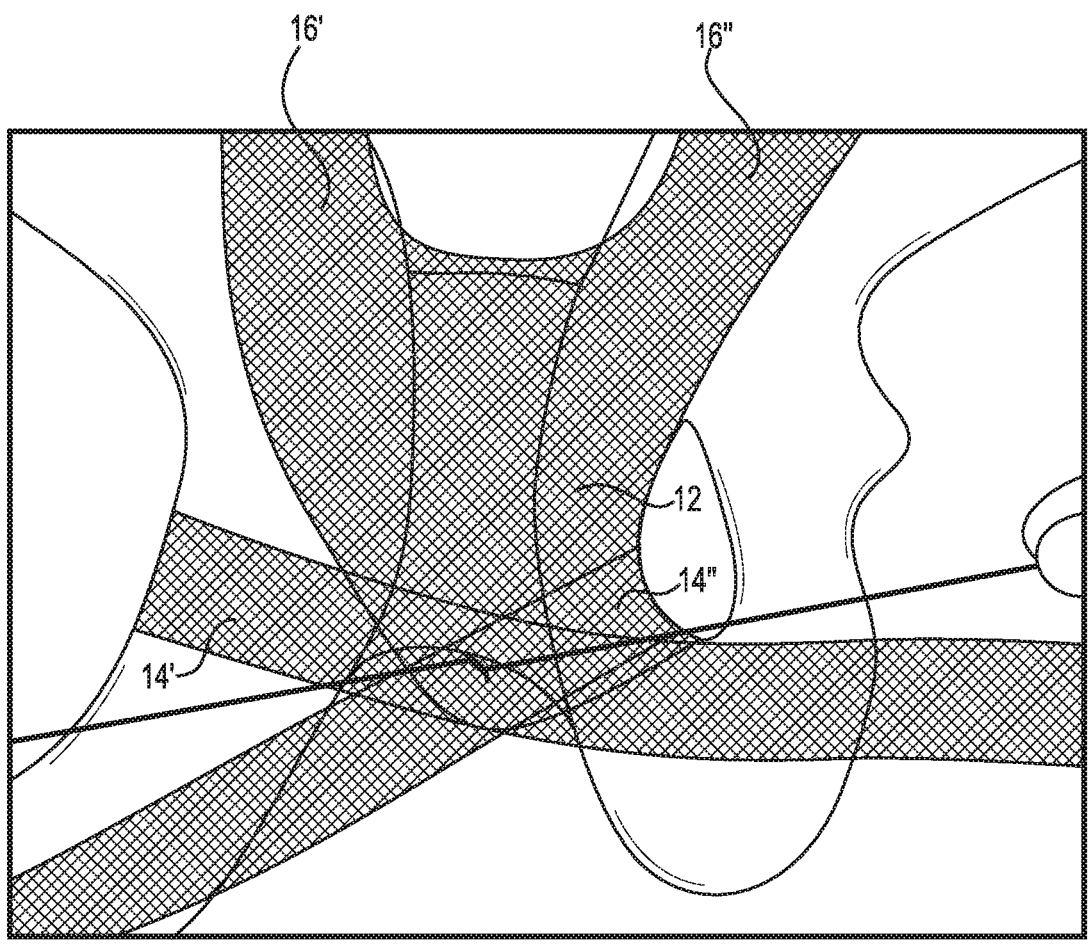
Figure 14:
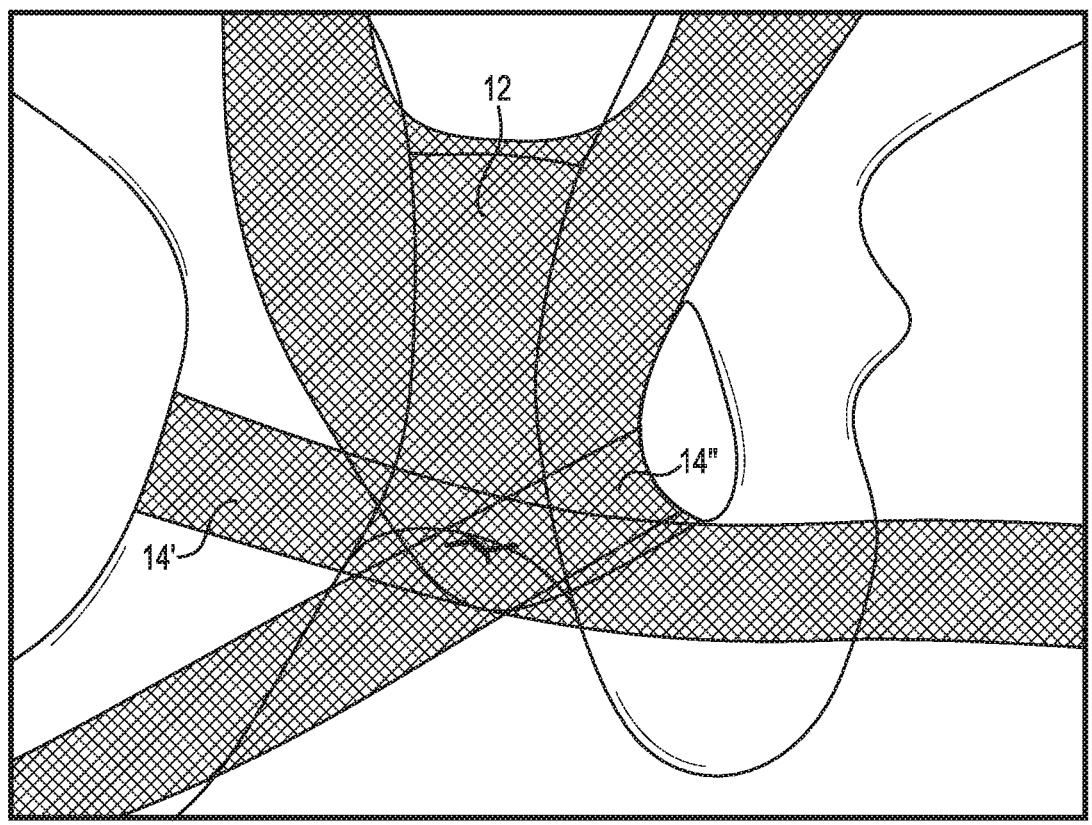
Figure 15:
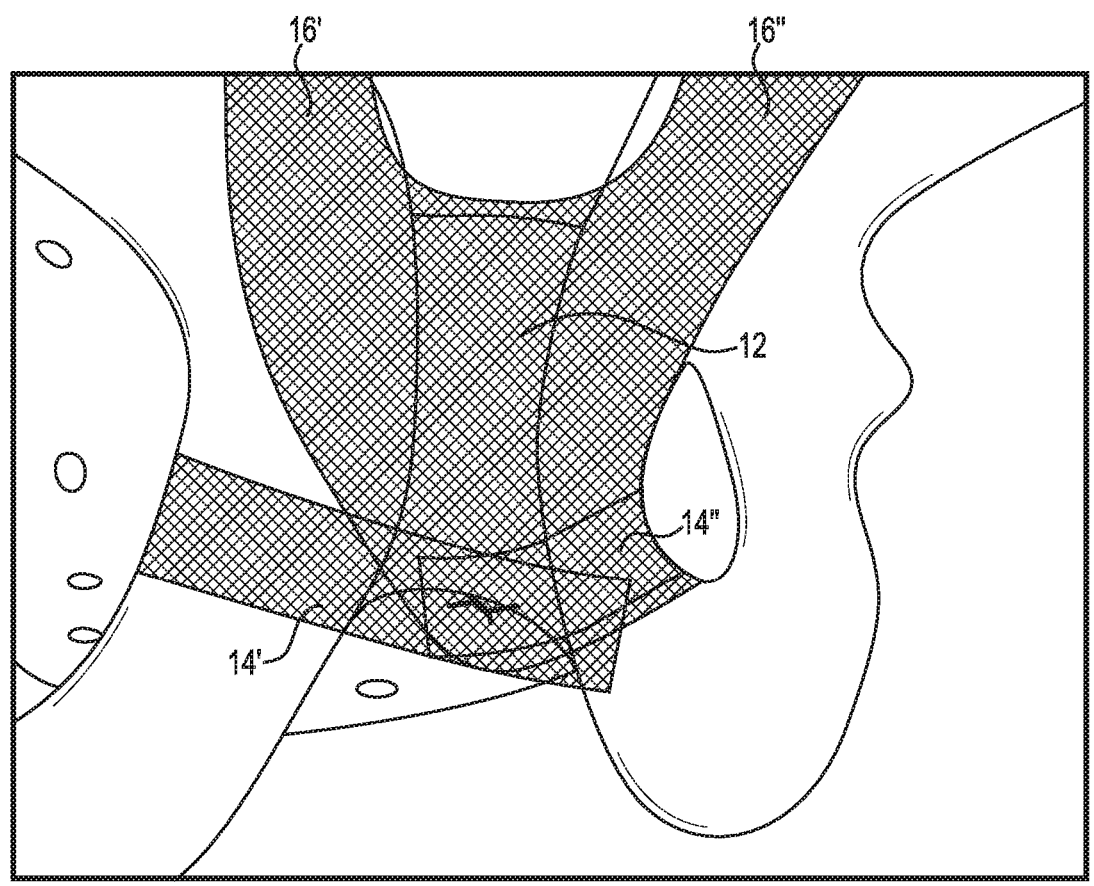

As shown in FIG. 10, the arms 14' and 14" of the device 10 should be placed and pulled to an extent that the bottom B of the body member 12 of the device 10 may be placed just inferior to the level of the bulbar urethral complex and over the pubic symphysis superiorly. The device 10 may be tensioned to achieve optimal compression. In order to fix the device 10 in a desired orientation, the arms 14', 14" of the device 10 should lie just inferior to the level of the bulbous urethra. In one embodiment, as shown in FIGS. 11-15, the arms 14', 14" are then secured with suture (e.g., prolene) to each other and excess lengths are trimmed off. In these example illustrations, it is to be understood that demonstration of the example method of the present invention by way of, as aforesaid, a model of a pelvic region including pelvic bone structure, is analogous to actual surgery on a patient. It is also to be understood that in several of these illustrations legs 16', 16" are draped over pelvic bone structure to allow an unimpeded view of the aforementioned steps with respect to the arms 14', 14".

Figure 16:
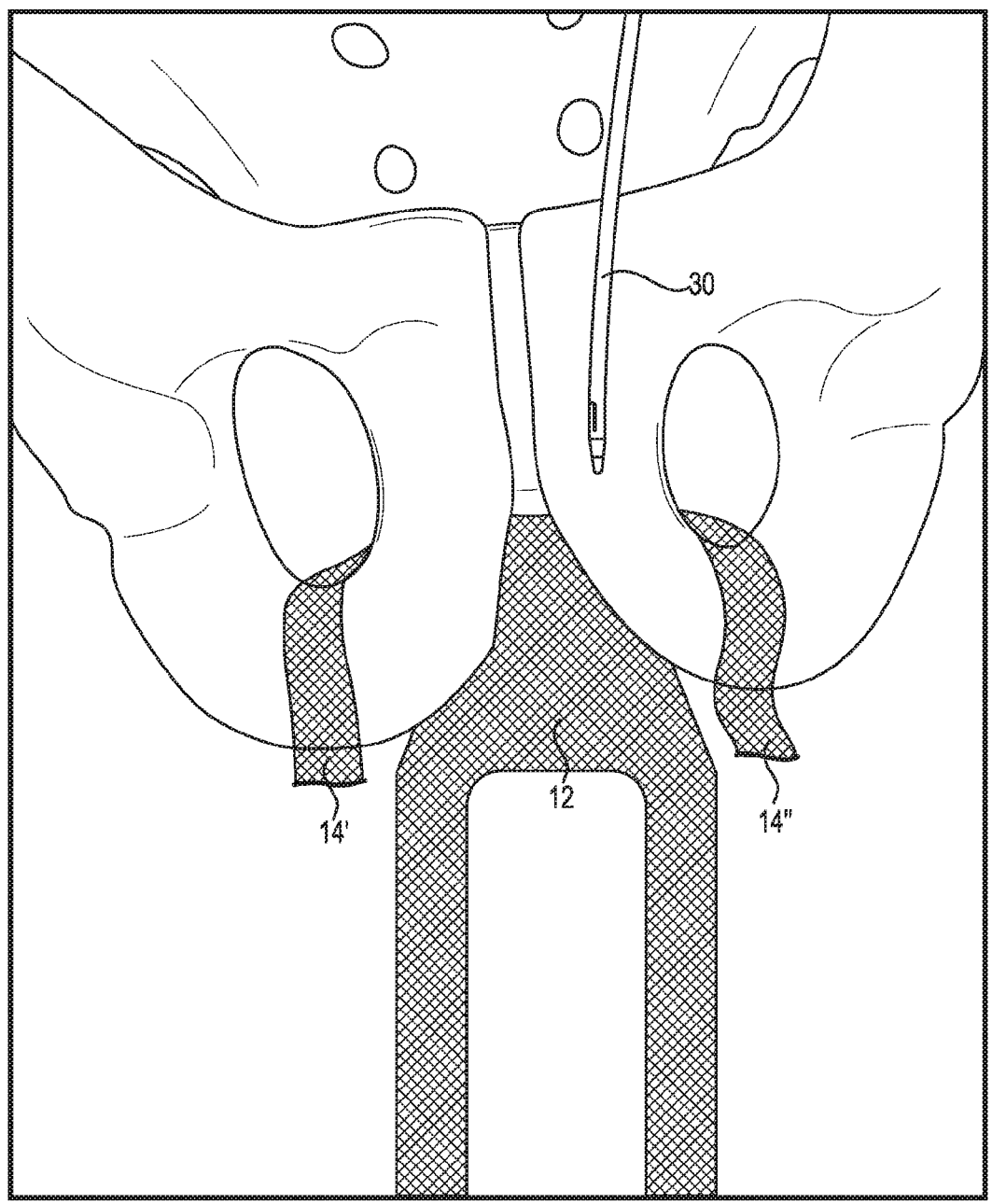
Figure 17:
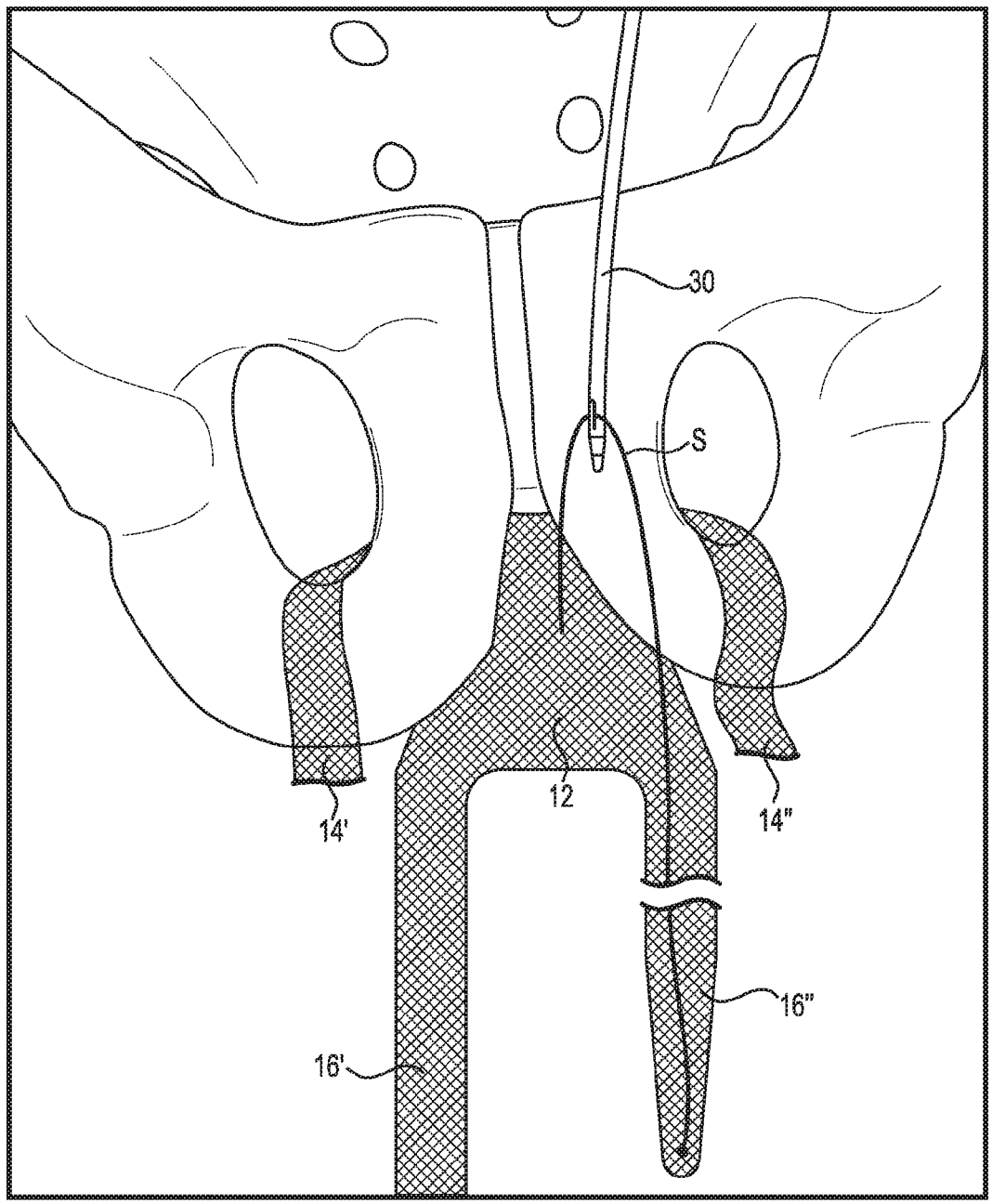
Figure 18:
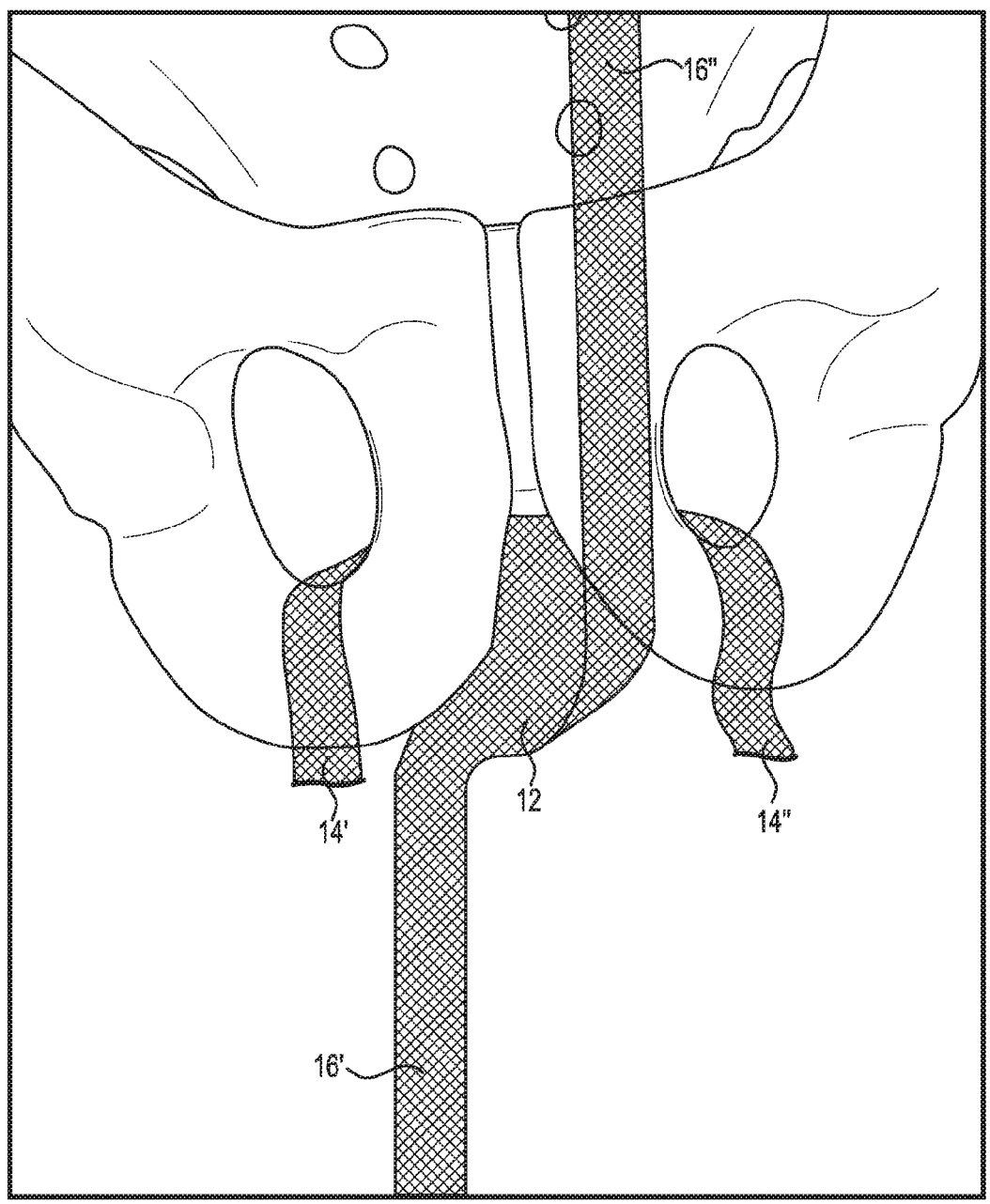
Figure 19:
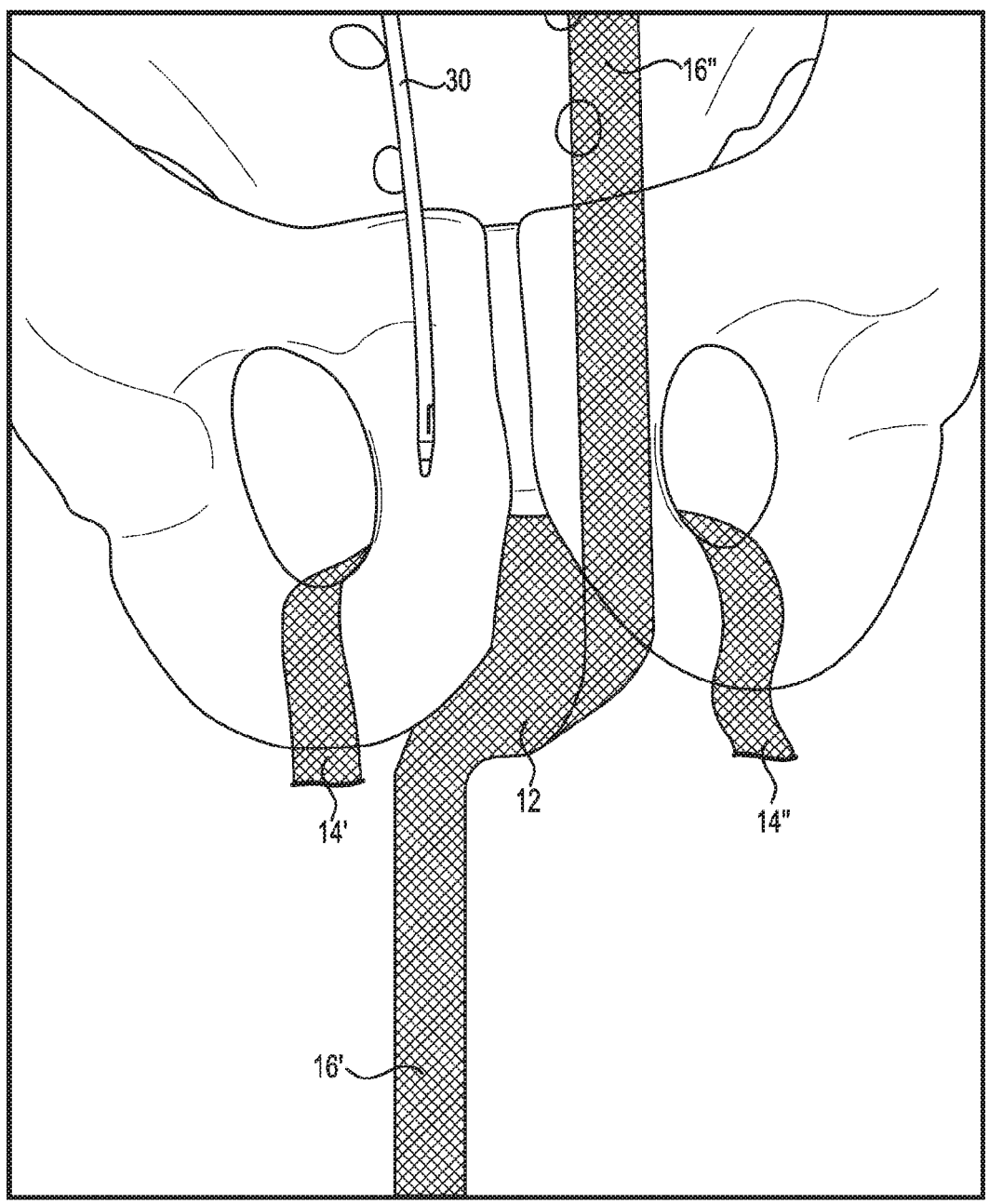
Figure 20:
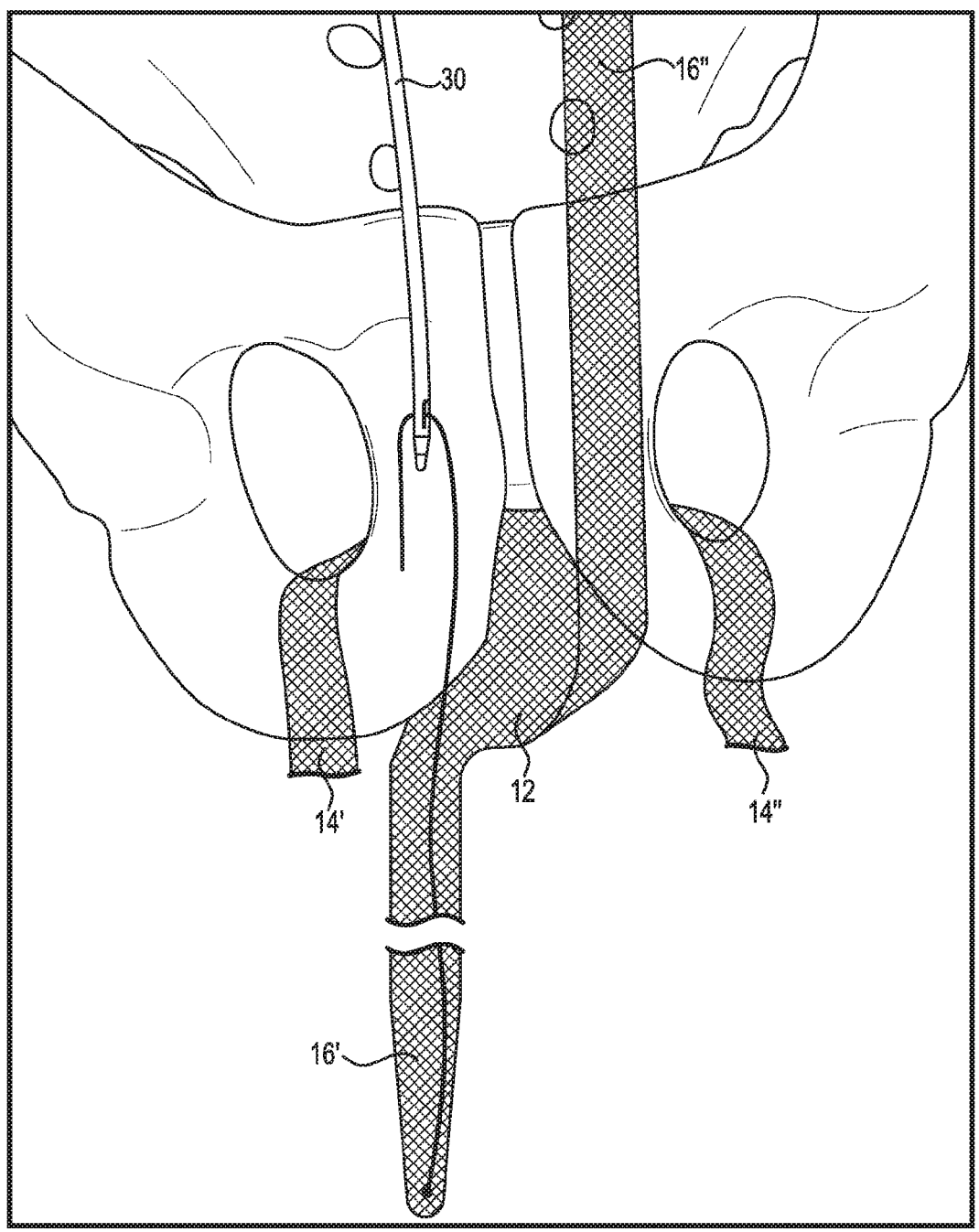
Figure 21:
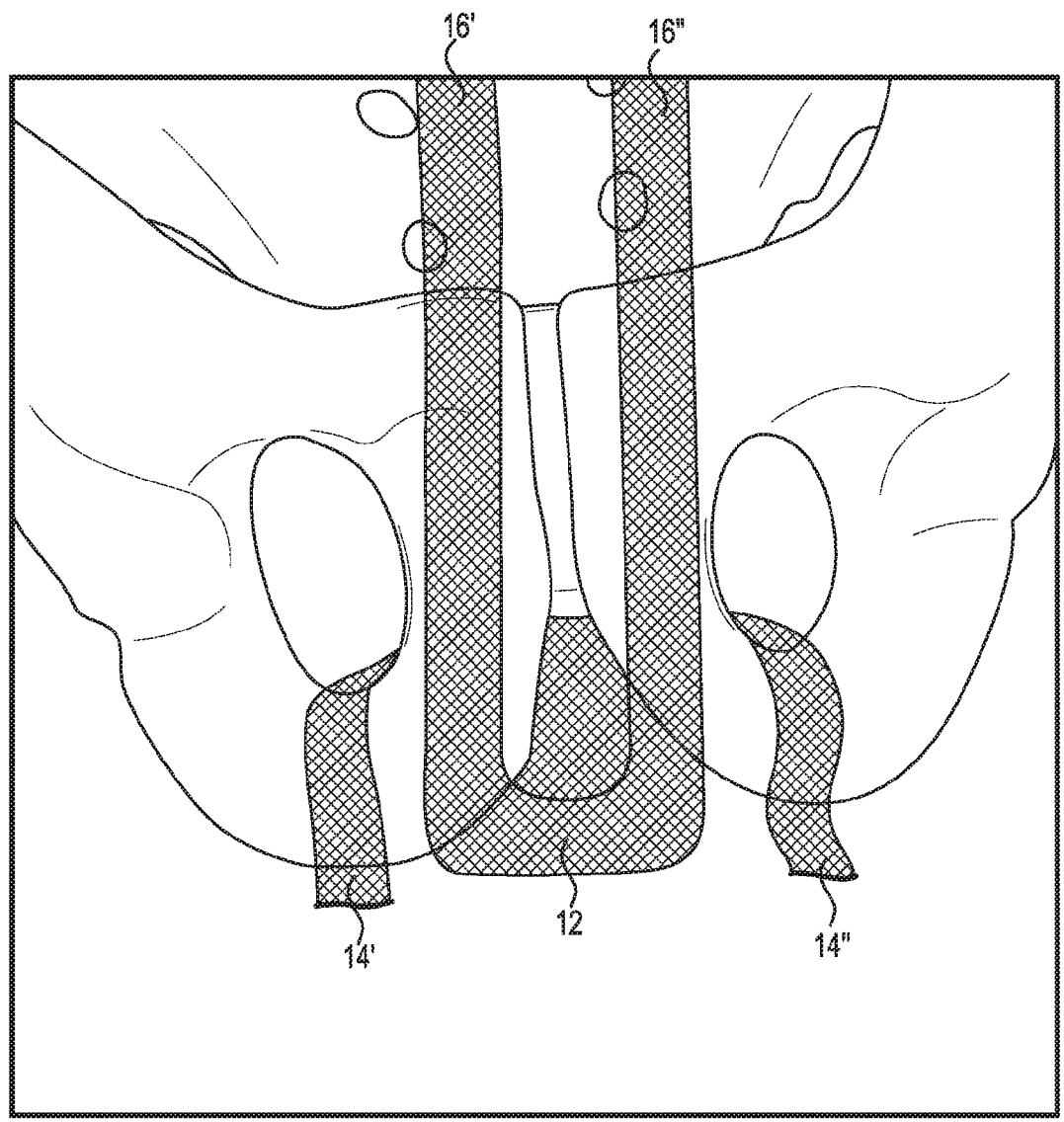
Figure 22:
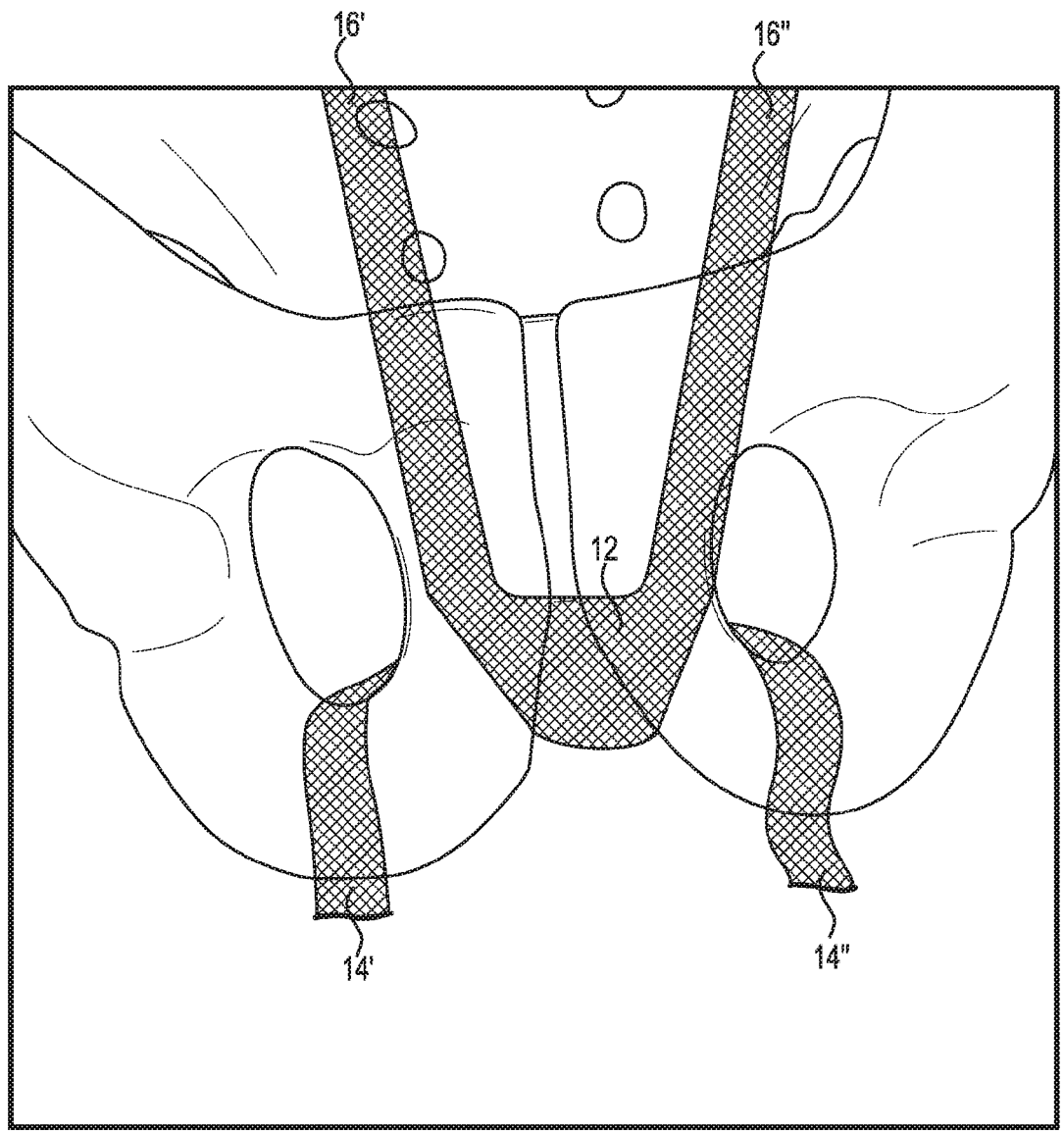

Thereafter to complete placement of the device 10 in an example of the surgical method of the present invention, an opposing pair of approximately 1 cm abdominal incisions is made approximately 3 cm above the pubic symphysis and approximately 3 cm lateral to the midline. As shown in FIG. 16, a suprapubic introducer 30 may be passed prepubically from above, entering a selected first one of the abdominal incisions and passed out through the initial perineal incision lateral to the periurethral tissue. Care should be taken to palpate the introducer tip 36 of the suprapubic introducer 30 with the non-dominant hand and to avoid the proximal crura high on the pubic ramus. As shown in FIGS. 17 and 18 (although arms 14', 14" are shown as not being secured, it is to be understood that they have been as aforedescribed relative to FIGS. 11-15) the leg 16" of the device 10 may be attached to the introducer 30, preferably by loading a suture S with the leg 16" or by any suitable technique of attaching the leg 16" to a portion proximal to the tip of the introducer 30 (e.g., by way of the aforedescribed slot 37) and pulled back out by reversing the pathway that the introducer 30 entered and, thereafter, out the abdominal incision. As shown in FIGS. 19, 20, and 21, these steps are repeated on the contra lateral side, with respect to the leg 16'. As shown in FIG. 22, the legs 16', 16" should be pulled such that the body member 12 of the device 10 may be over the pubic symphysis superiorly.

Figure 23:
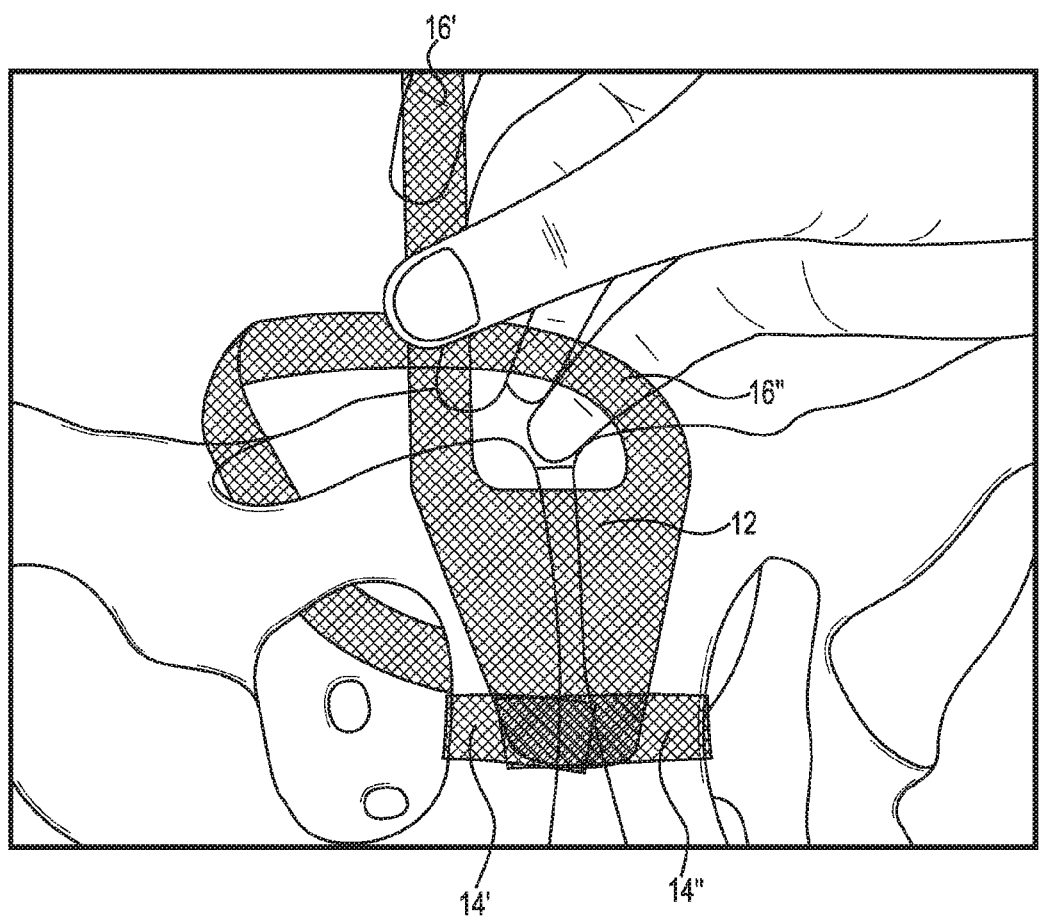
Figure 24:
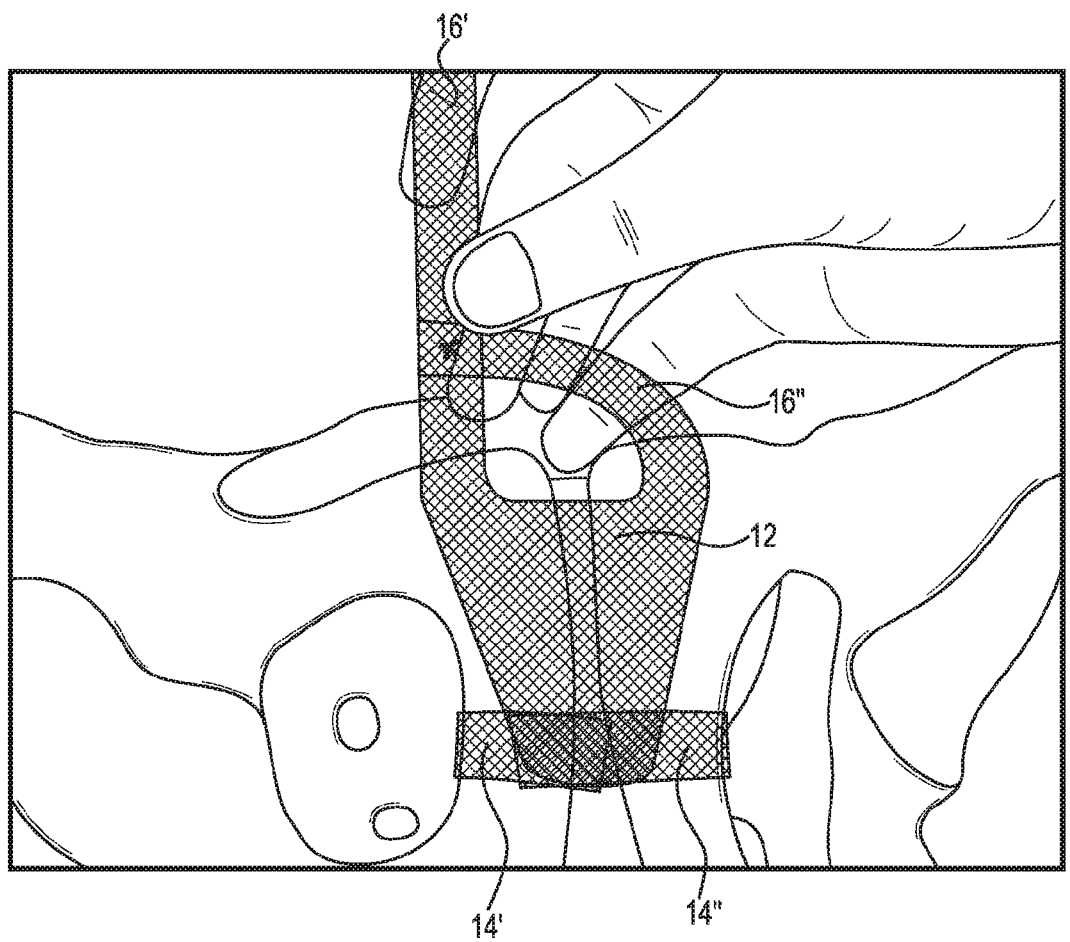
Figure 25:
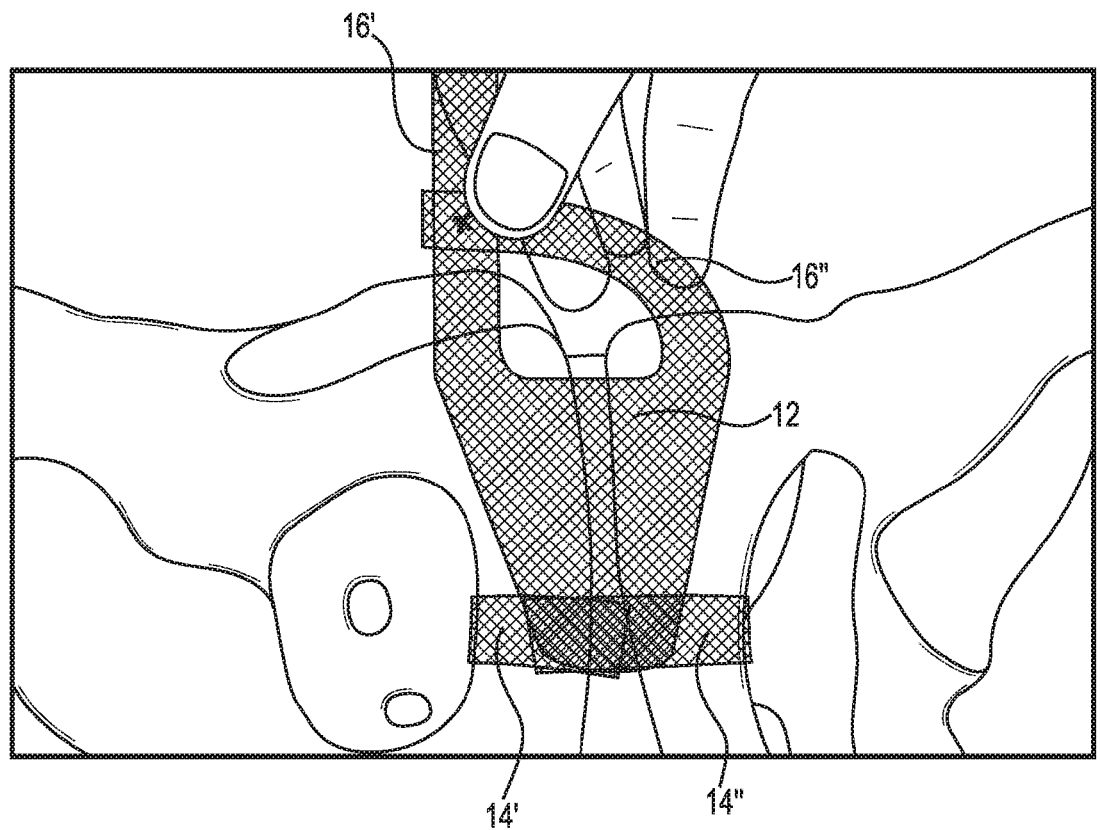
Figure 26:
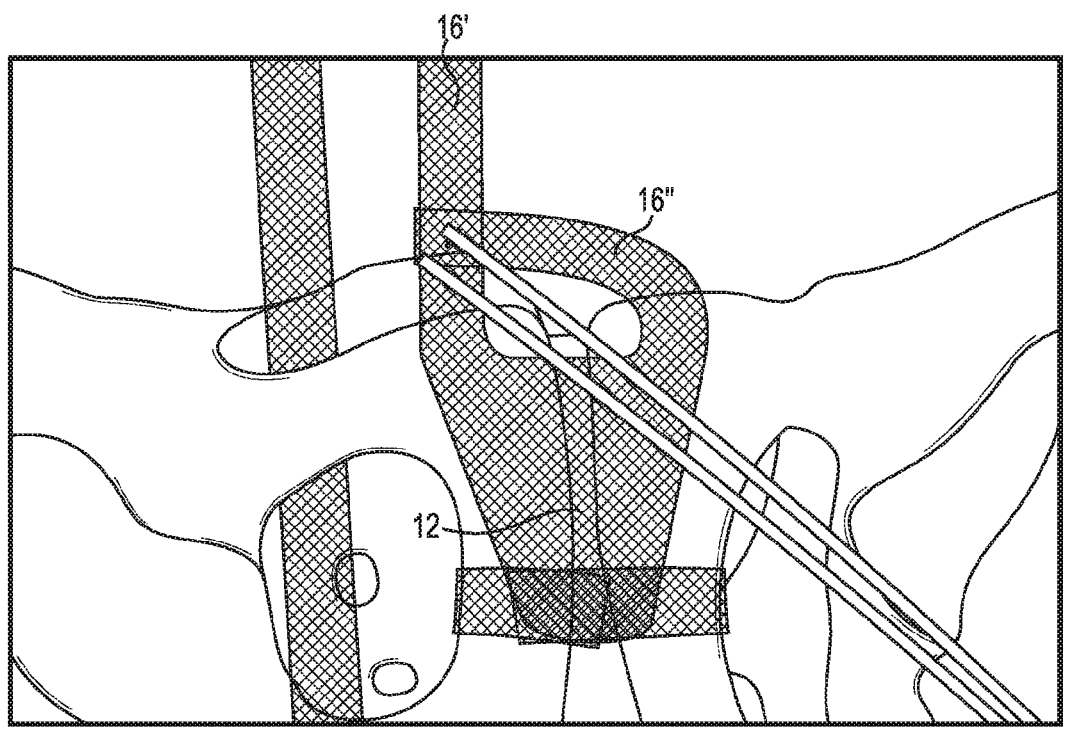
Figure 27:
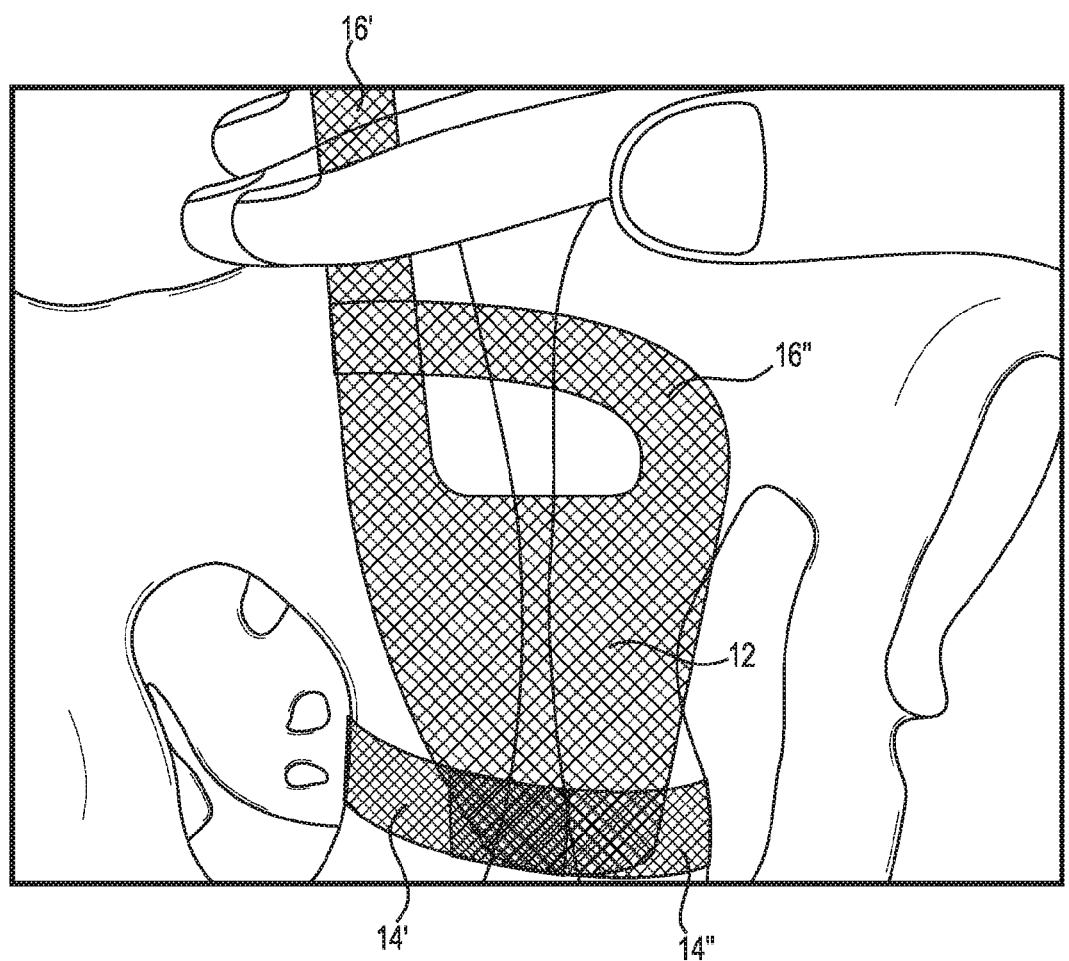
Figure 28:
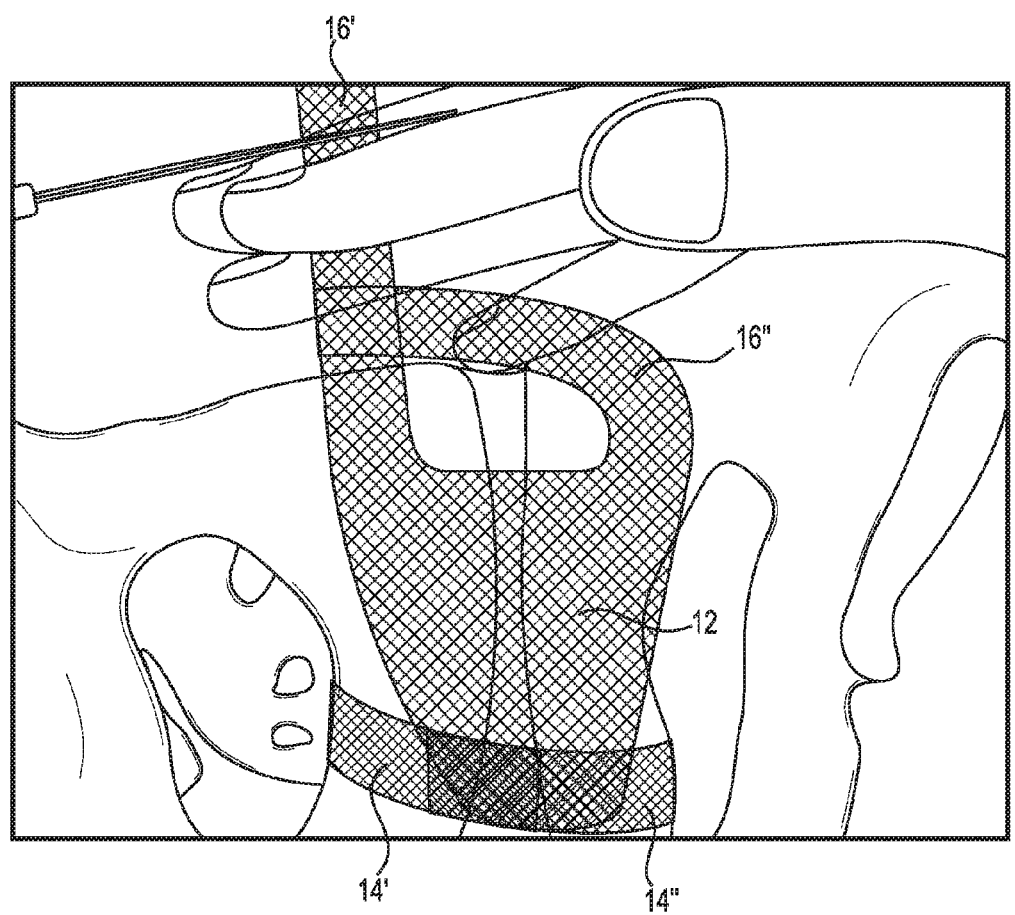
Figure 29:
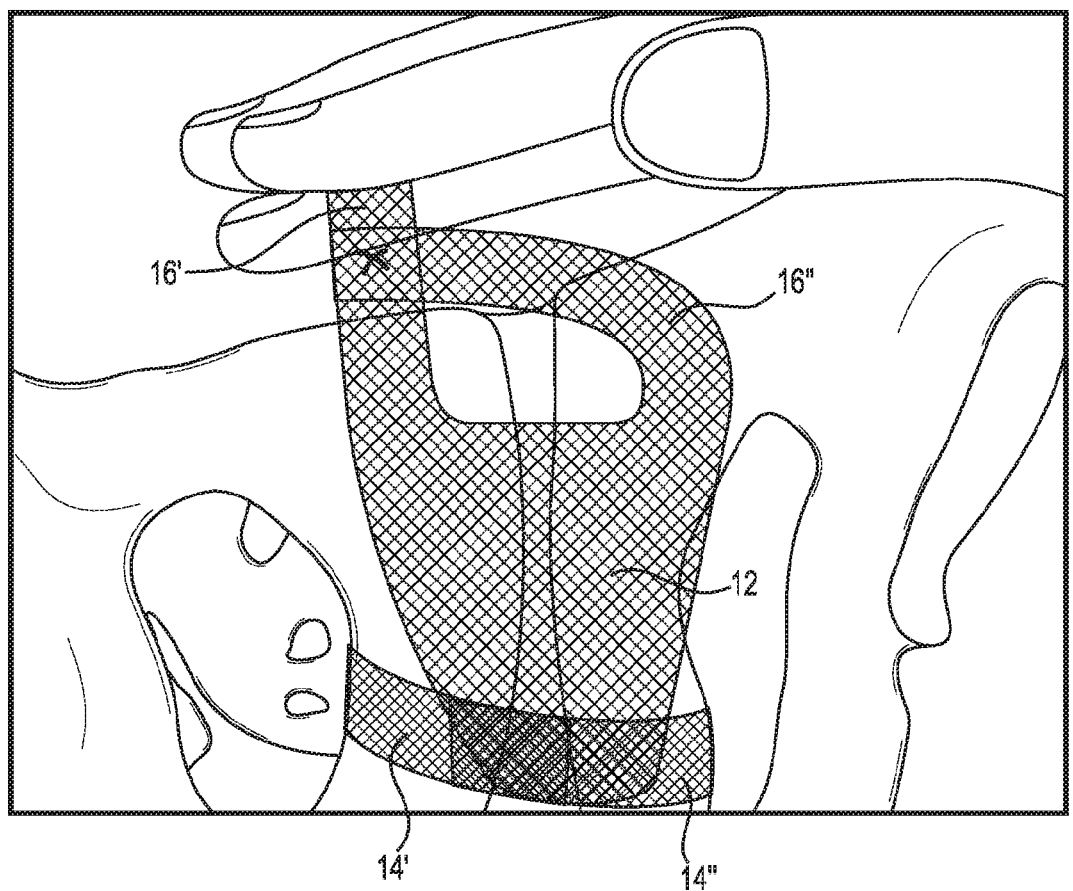

With the arms 14', 14" of the device 10 secured, in one example embodiment as shown in FIG. 23 a selected one of the legs 16', 16" of the device 10 may be thereafter passed under the patient's skin (e.g., "tunneled over") to the other leg. The legs 16', 16" are then tensioned to achieve an optimal desired compression of the device 10. The other, non-tunneled leg may then be anchored subcutaneously via securing that leg just below the level of the patient's skin. It is to be appreciated, however, that the legs 16', 16" may be secured within the patient's body by various means. In one embodiment, the legs 16', 16" may be tied together. In another embodiment, as shown in FIGS. 24, 25, 26, 27, 28, and 29, the legs 16', 16" may be sutured together and excess lengths are trimmed off. In yet another embodiment, one or both of the legs 16', 16" may be sutured to the body member 12 of the device 10. In yet another embodiment, one or both of the legs 16', 16" may be left free-flowing within the patient's body cavity, thereby engaging the surrounding tissue and permitting fibroblast infiltration to further tension and secure them within the patient's body cavity. The previously mentioned embodiments regarding securing the legs may be used independently or in combination with one another to achieve optimal tensioning of the device 10. Once the legs 16', 16" have been tensioned as desired, any excess lengths thereof and/or sutures may be trimmed to a desired length to allow for any necessary postoperative adjustments.

Figure 30:
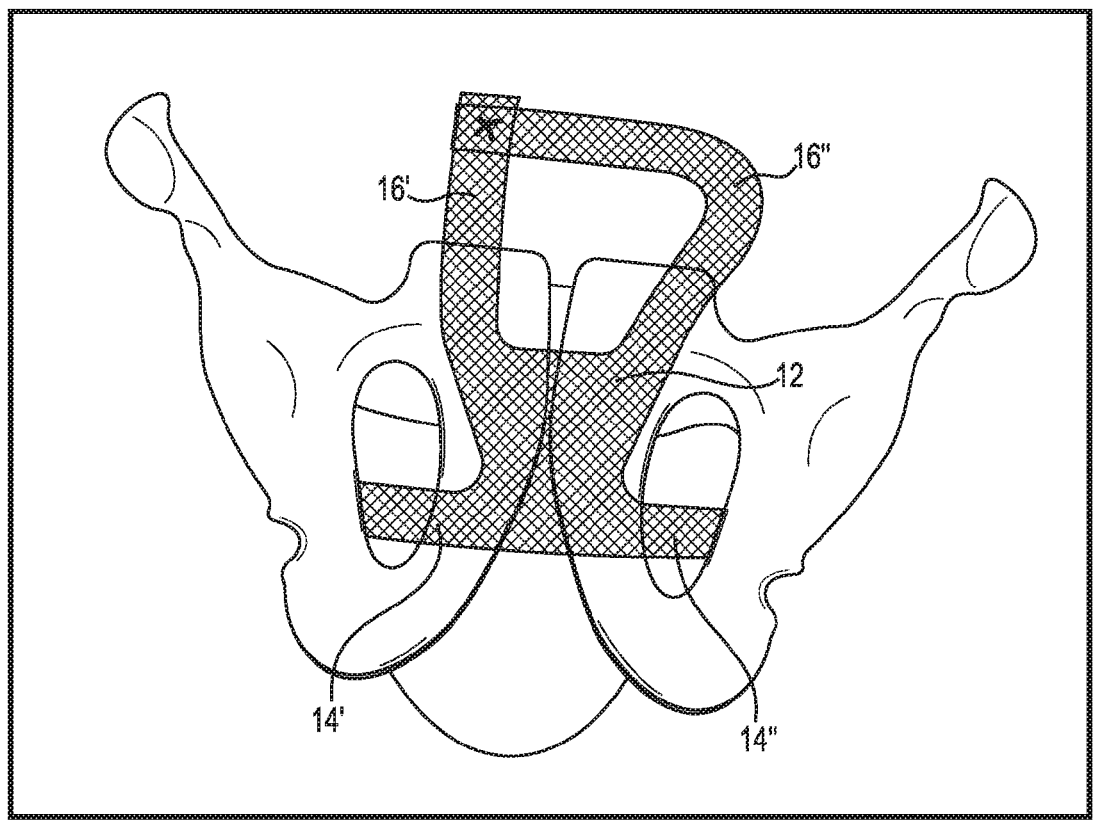

As shown in FIG. 30, the legs 16', 16", as described above, may be adjusted postoperatively to correct any remaining degree of incontinence. The legs 16', 16" of the device 10 may lie over the pubic symphysis superiorly. The arms 14, 14" and legs 16', 16" may be tensioned to achieve optimal compression of the device 10.

During a follow-up visit to the surgeon, the surgeon may be able to evaluate the patient for postoperative continence. Because of the adjustability of the device 10, should the patient have some leakage postoperatively the surgeon may be able to make a small incision in the lower abdomen where the two legs 16', 16" of the device 10 were placed. The surgeon will then pull up on selected ones of the two exposed legs 16', 16"—thus pulling up on the entire device 10 and creating greater lift on the urethra, thereby eliminating any further leakage that might occur. The two legs 16', 16" may then be re-secured to preserve this new tightness. In similar manner, should a patient be in retention from the surgeon placing the legs too tightly, the surgeon may be able to cut the suture and retie or otherwise re-secure the legs so that the tension may be reduced. The postoperative adjustment can be done in a physician's office or in an outpatient setting rather than via hospital admittance and administration of a general anesthetic to the patient.

It is to be particularly appreciated and understood that, in a fundamental sense, the treatments of urinary incontinence in accordance with the present invention utilize a suitable implantable device to provide desired pressure on, or compression of, a patient's bulbar urethral complex. This desired effect on the urethral complex is basically achieved, regardless of a particular device, method, or tools, by providing an implantable device having a body member defining a top and a bottom, at least first and second elongated extension members, and at least third and fourth elongated extension members. The at least first and second elongated extension members are placed so that the bottom of the body member is located proximal to the bulbar urethral complex and over a pubic symphysis of the patient, superiorly. The at least first and second elongated extension members are secured by way of the obturator foramen; these structures of the patient's pelvic region provide a locus at which at least a portion of the body member is substantially fixed in spatial relationship to the obturator foramen and the patient's overall pelvic region. The at least third and fourth elongated extension members are placed such that the body member of the device is over the pubic symphysis, superiorly. The at least third and fourth elongated extension members are then secured within the patient's body and are utilized to provide desired tensioning of the device with respect to the bulbar urethral complex upon which it is acting.

Although the invention has been described in terms of particular embodiments and applications, one of ordinary skill in the art, in light of the teaching, can generate embodiments and modifications without departing from the spirit of, or exceeding the scope of, the claimed invention. For example, it will be clear to one of ordinary skill in the art how to apply the inventive concepts disclosed herein to the treatment of female incontinence. Accordingly, it is to be understood that the drawings and descriptions herein are proffered by way of example to facilitate comprehension of the invention and should not be construed to limit the scope thereof.

While the present invention has been particularly shown and described with reference to the accompanying specification and drawings, it will be understood however that other modifications thereto are of course possible; and all of which are intended to be within the true spirit and scope of the present invention. For example, introducers in forms of trocars and cannulas could be equally utilized herein, instead of the solid, needle-like introducers as shown and described.

It should be appreciated that (i) components, dimensions, and other particulars of example embodiments of the invention aforedescribed may be substituted for others that are suitable for achieving desired results, (ii) various additions or deletions may be made thereto, and (iii) features of the foregoing examples may also be made in combinations thereof. It is also to be understood in general that any suitable alternatives may be employed to provide the implantable devices, surgical methods, and surgical tools of the present invention.

Lastly, of course, the choice of compositions, sizes, and strengths of various aforementioned elements of the present invention are all a matter of design choice depending upon intended uses thereof. Accordingly, these and other various changes or modifications in form and detail of the present invention may also be made therein, again without departing from the true spirit and scope of the invention as defined by the appended claims.

What is claimed is:

1. A method for treating urinary incontinence in a male patient, the method comprising:
providing an implantable device having a support portion including an upper portion and a lower portion, first and second arms that are parallel with one another and first and second legs that are parallel with one another and extend in a direction that is orthogonal to the first and second arms;
making a perineal incision in a male patient;
providing an introducer having an introducer tip;
attaching a portion of the first arm to the introducer tip and passing the introducer tip through a first obturator foramen and the perineal incision to pass the first arm through the first obturator foramen;
attaching a portion of the second arm to the introducer tip and passing the introducer tip through a second obturator foramen and the perineal incision to pass the second arm through the second obturator foramen;
extending the support portion upward to the pubic bone of the male patient and positioning the first pubic rami in a first recess located below the first arm and positioning the second pubic rami in a second recess located below the second arm, the first recess being formed by a first edge and a second recess being formed by a second edge of the support portion, each of the first edge and the second edge, respectively, extending inwardly toward a center of the support portion below the first and second arms and then outwardly from the center of the support toward the lower portion; and
tensioning the first and second arms to achieve suburethral compression.

2. The method of claim 1, wherein the support portion is trapezoidal in shape and extending the support portion upward to the pubic bone of the male patient comprises extending the relatively wider portion of the trapezoidal shape under the bulbar urethra and upward to the pubic bone of the male patient.

3. A method for treating urinary incontinence in a male patient, the method comprising:
providing an implantable device having a support portion including an upper portion and a lower portion, a first arm extending from the support portion, and a second arm that extends from the support portion in a parallel direction to the first arm;
making a perineal incision in a male patient;
providing an introducer having an introducer tip;
attaching a portion of the first arm to the introducer tip and passing the introducer tip through a first obturator foramen and the perineal incision to pass the first arm through the first obturator foramen;

attaching a portion of the second arm to the introducer tip and passing the introducer tip through a second obturator foramen and the perineal incision to pass the second arm through the second obturator foramen;

extending the support portion upward to the pubic bone of the male patient;

securing the support portion to the pubic bone of the male patient and positioning the first pubic rami in a first recess located below the first arm and positioning the second pubic rami in a second recess located below the second arm, the first recess formed by a first edge of the support portion extending inwardly toward a center of the support below the first arm and then outwardly from the center of the support portion toward the lower portion, and a second recess formed by a second edge of the support portion extending inwardly toward the center of the support below the second arm and then outwardly from the center of the support portion toward the lower portion; and tensioning the first and second arms to achieve suburethral compression.

4. The method of claim 3, wherein securing the support portion to the pubic bone of the patient includes securing the support portion to periosteum tissue of the pubic bone.

5. The method of claim 3, wherein securing the support portion to the pubic bone of the patient includes securing the support portion to tissue of the pubic bone.

6. The method of claim 3, wherein securing the support portion to the pubic bone of the patient includes tacking the support portion to the pubic bone.

7. The method of claim 3, wherein securing the support portion to the pubic bone of the patient includes suturing the support portion to tissue of the pubic bone.

8. The method of claim 3, wherein securing the support portion to the pubic bone of the patient includes passing one or more anchor elements through one or more preformed apertures in the support portion.

9. The method of claim 3, wherein securing the support portion to the pubic bone of the patient includes passing one or more sutures through one or more preformed apertures in the support portion and into tissue of the pubic bone.

10. The method of claim 9, wherein the support portion is trapezoidal in shape, the method further comprising extending the relatively wider portion of the trapezoidal shape under the bulbar urethra and upward to the pubic bone of the male patient.

* * * * *